(12) United States Patent
Pratt et al.

(10) Patent No.: US 12,239,779 B2
(45) Date of Patent: Mar. 4, 2025

(54) LOW PROFILE INSTILLATION AND NEGATIVE-PRESSURE BRIDGE

(71) Applicant: Solventum Intellectual Properties Company, Maplewood, MN (US)

(72) Inventors: Benjamin Andrew Pratt, Poole (GB); Justin Rice, Denver, CO (US); Thomas Alan Edwards, Hampshire (GB); Christopher Allen Carroll, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 309 days.

(21) Appl. No.: 17/599,855

(22) PCT Filed: Mar. 20, 2020

(86) PCT No.: PCT/US2020/023910
§ 371 (c)(1),
(2) Date: Sep. 29, 2021

(87) PCT Pub. No.: WO2020/210002
PCT Pub. Date: Oct. 15, 2020

(65) Prior Publication Data
US 2022/0193327 A1    Jun. 23, 2022

Related U.S. Application Data

(60) Provisional application No. 62/830,984, filed on Apr. 8, 2019.

(51) Int. Cl.
*A61M 1/00* (2006.01)
*A61F 13/05* (2024.01)
(Continued)

(52) U.S. Cl.
CPC ............. *A61M 1/964* (2021.05); *A61F 13/05* (2024.01); *A61M 1/85* (2021.05); *A61M 1/92* (2021.05);
(Continued)

(58) Field of Classification Search
CPC .......... A61M 39/105; A61M 2039/082; A61M 1/0086; A61M 3/0279; A61M 1/0084;
(Continued)

(56) References Cited

U.S. PATENT DOCUMENTS 1,355,846 A    10/1920  Rannells
2,547,758 A    4/1951   Keeling
(Continued)

FOREIGN PATENT DOCUMENTS

AU    550575 B2    3/1986
AU    745271 B2    3/2002
(Continued)

OTHER PUBLICATIONS

Chinese Office Action for corresponding application 2020800270983, dated Aug. 31, 2023.
(Continued)

*Primary Examiner* — Kai H Weng
*Assistant Examiner* — Alessandro R Del Priore

(57) ABSTRACT

Disclosed embodiments relate to devices and systems for providing both negative-pressure therapy and instillation, In some embodiments, both negative-pressure and instillation may be provided to a tissue site in a low-profile context that may also prevent siphoning of instillation fluid during negative pressure application. For example, a single bridge may include a negative-pressure pathway with supports and an instillation pathway, and the instillation pathway may be configured with respect to the negative-pressure pathway so that at least a portion of the instillation pathway collapses
(Continued)

upon application of negative pressure to the negative-pressure pathway. Collapse of at least a portion of the installation pathway may be sufficient to close the installation pathway.

15 Claims, 23 Drawing Sheets

(51) Int. Cl.
  *A61M 3/02* (2006.01)
  *A61M 39/22* (2006.01)
(52) U.S. Cl.
  CPC ............ *A61M 1/96* (2021.05); *A61M 3/0233* (2013.01); *A61M 39/227* (2013.01)
(58) Field of Classification Search
  CPC ...... A61M 1/0088; A61M 39/00; A61M 1/90; A61F 13/00068; A61F 13/0216; A61F 13/0253; A61F 2013/00174; A61F 2013/0028; A61P 17/02
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0160877 A1* | 6/2010 | Kagan ................ A61F 13/0203 604/319 |
| 2011/0184362 A1* | 7/2011 | Croizat ................ A61M 1/915 604/319 |
| 2013/0053797 A1* | 2/2013 | Locke ................ A61M 1/966 604/319 |
| 2014/0163491 A1 | 6/2014 | Schuessler et al. |
| 2014/0330224 A1* | 11/2014 | Albert ................ A61F 13/0206 604/319 |

(56) References Cited

U.S. PATENT DOCUMENTS

| | | | |
|---|---|---|---|
| 2015/0080788 A1 | 3/2015 | Blott et al. | |
| 2016/0199550 A1* | 7/2016 | Seddon | A61F 13/00068 604/319 |
| 2017/0007751 A1* | 1/2017 | Hartwell | A61M 1/91 |
| 2017/0028113 A1* | 2/2017 | Shuler | A61M 1/915 |
| 2018/0028365 A1 | 2/2018 | Albert et al. | |
| 2018/0311418 A1* | 11/2018 | Hartwell | A61M 1/85 |
| 2018/0311420 A1* | 11/2018 | Cotton | A61M 1/915 |
| 2018/0361038 A1* | 12/2018 | Croizat | A61M 1/77 |
| 2019/0022289 A1 | 1/2019 | Pratt et al. | |
| 2019/0321232 A1* | 10/2019 | Jardret | A61F 13/00068 |

FOREIGN PATENT DOCUMENTS

| | | |
|---|---|---|
| AU | 755496 B2 | 12/2002 |
| CA | 2005436 A1 | 6/1990 |
| CN | 207341956 U | 5/2018 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3 169 382 A1 | 5/2017 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| JP | 2012090879 A | 5/2012 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0007653 A1 | 2/2000 |
| WO | 2005046762 A1 | 5/2005 |
| WO | 2009125387 A2 | 10/2009 |
| WO | 2016015001 A2 | 1/2016 |
| WO | WO-2017205556 A1 * | 11/2017 |
| WO | 2017/209945 A1 | 12/2017 |

OTHER PUBLICATIONS

International Search Report and Written Opinion for Corresponding Application No. PCT/US2020/023910 mailed Aug. 24, 2020.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sept. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.

(56) References Cited

OTHER PUBLICATIONS

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Japanese Notice of Rejection for corresponding application 2021-559573, dated Mar. 12, 2024.
Chinese Office Action for corresponding application 2020800270983, issued Mar. 30, 2024.

* cited by examiner

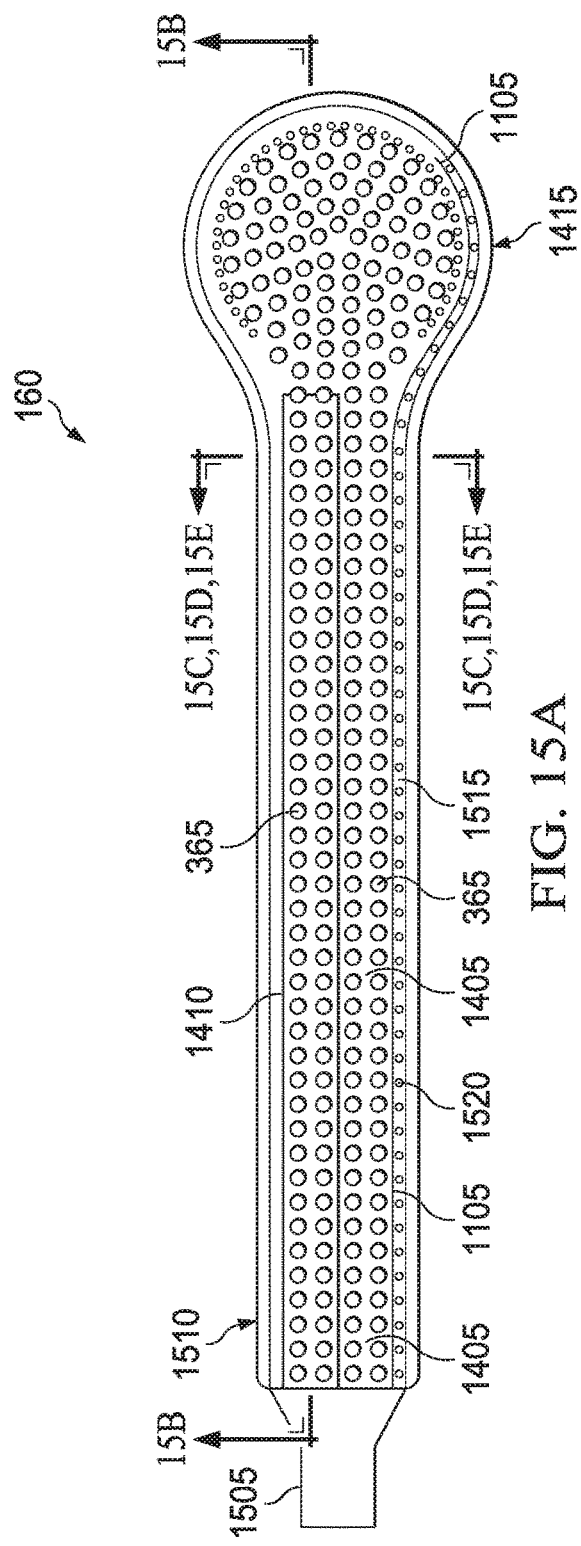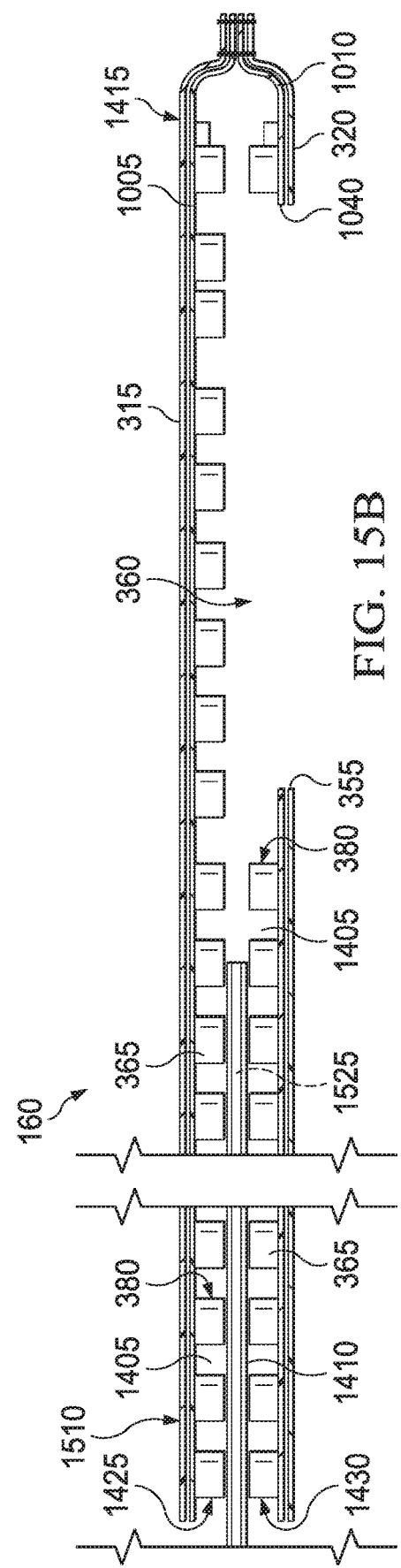
FIG. 15A
FIG. 15B

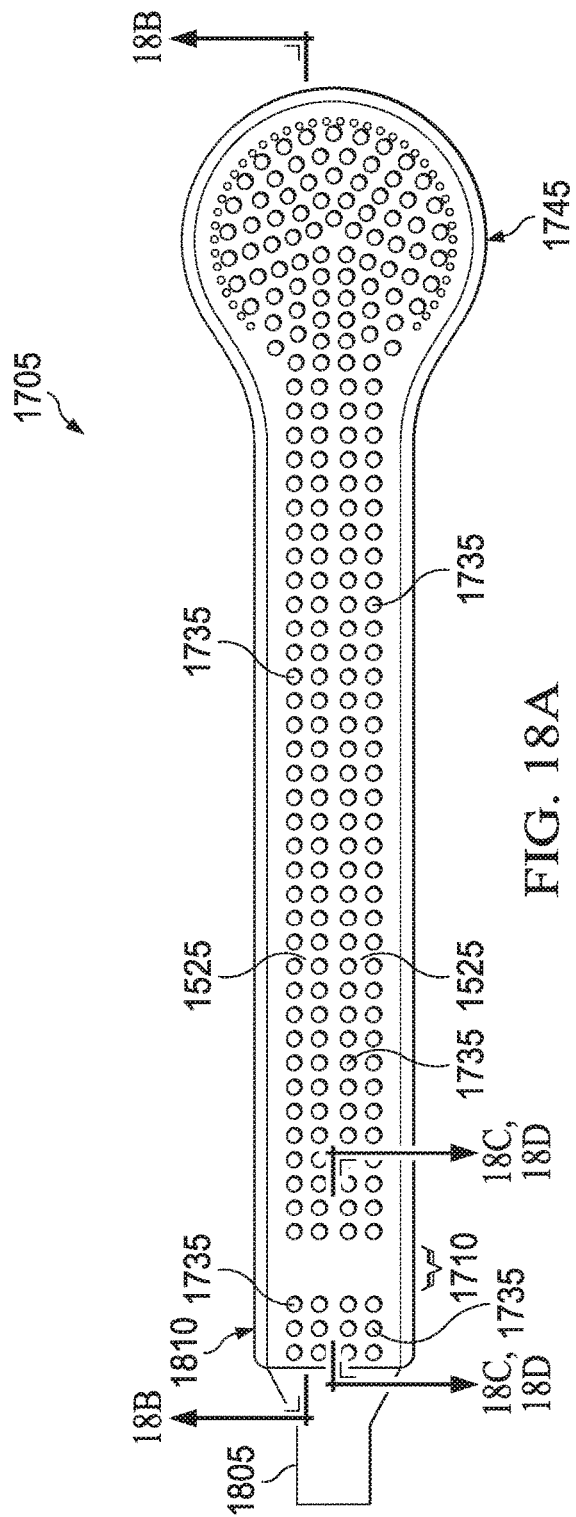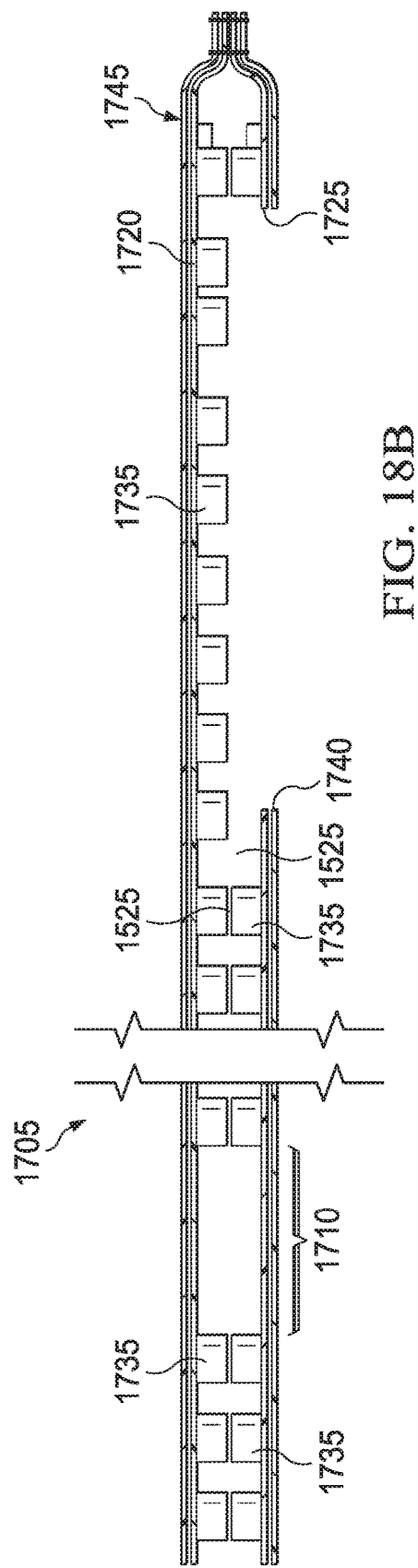
FIG. 18A
FIG. 18B

LOW PROFILE INSTILLATION AND NEGATIVE-PRESSURE BRIDGE

RELATED APPLICATIONS

The present application claims priority to U.S. Provisional Patent Application No. 62/830,984, entitled "Low Profile Installation and Negative-Pressure Bridge," filed Apr. 8, 2019, which is incorporated herein by reference for all purposes.

TECHNICAL FIELD

The invention set forth in the appended claims relates generally to tissue treatment systems and more particularly, but without limitation, to low-profile distribution components for providing negative-pressure therapy and/or instillation.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter. Some embodiments are illustrative of an apparatus or system for delivering both negative pressure and instillation to a tissue site, which can be used in conjunction with low-profile distribution components.

For example, in some embodiments, a low-profile bridge may be configured to allow application of negative pressure and instillation fluid alternately, through separate pathways. The configuration may maintain an open pathway for the application of both negative pressure and instillation fluid, which does not occlude even if a compressive load is applied to the bridge. Further, the configuration may prevent unintended siphoning of the instillation fluid during negative-pressure therapy. For example, a single bridge may include two separate pathways: a negative-pressure pathway and an instillation pathway. In some embodiments, the instillation pathway may be a collapsible conduit located within the negative-pressure pathway. For example, the instillation pathway may comprise a thin polyurethane tube. The negative-pressure pathway may include open pathway features, configured to maintain an open pathway in the negative-pressure pathway. For example, the open pathway features may be thermoformed structures, which may include a plurality of supports configured to prevent collapse of the negative-pressure pathway in some embodiments. In some embodiments, the negative-pressure pathway may locate these thermoformed structures within a barrier film shell that is sealed to provide an enclosed pathway for negative pressure. The supports of the negative-pressure pathway may contact the collapsible instillation conduit in some embodiments. For example, the negative-pressure pathway may comprise two stacked thermoformed structures, with supports from each thermoformed structure projecting into the enclosed space of the negative-pressure pathway from opposite directions, and in some embodiments the collapsible instillation conduit may be located between opposing supports in the negative-pressure pathway. In some embodiments, the instillation pathway and the negative-pressure pathway may be in fluid communication through their distal ends. For example, application of negative pressure to the negative-pressure pathway may collapse the instillation pathway, preventing or restricting fluid flow through the instillation pathway in order to prevent or reduce unintended siphoning of instillation fluid through the instillation pathway during negative-pressure wound therapy.

In some alternate embodiments, the instillation pathway may be located in a separate bridge from the negative-pressure pathway. For example, the instillation bridge may comprise open pathway features, such as instillation supports, to prevent collapse of the instillation pathway, but may have an unsupported section or gap which is configured to collapse upon experiencing negative pressure. The unsupported gap may be configured to be forced open during fluid delivery through the instillation pathway, but to close or clamp shut during fluid removal though the separate negative-pressure bridge. For example, the negative-pressure pathway may be located in a first low-profile bridge, while the instillation pathway may be located in a separate, second low-profile bridge. The instillation bridge and the negative-pressure bridge may be in fluid communication, so that during negative-pressure therapy through the negative-pressure pathway, the instillation pathway also experiences negative pressure. Applying negative pressure to the instillation pathway may act upon the gap to close the instillation pathway during negative-pressure wound therapy. The separate negative-pressure and instillation bridges may operate together as a system configured to provide negative-pressure therapy and/or instillation.

More generally, some embodiments may relate to managing fluid at a tissue site, and may comprise a negative-pressure pathway comprising a plurality of supports configured to support the negative-pressure pathway; and an instillation pathway configured to interact with the negative-pressure pathway so that at least a portion of the instillation pathway collapses upon application of negative pressure to the negative-pressure pathway. In some embodiments, the plurality of supports may be configured to maintain the negative-pressure pathway as an open pathway when the negative-pressure pathway is under compression. In some embodiments, the negative-pressure pathway and the instillation pathway may be pneumatically isolated from each other and the ambient environment except through an aperture and/or recessed space in a distal end of the apparatus. Collapse of the instillation pathway may be sufficient to close the instillation pathway, substantially preventing fluid flow through the instillation pathway in some embodiments. For example, the instillation pathway may comprise a collapsible conduit configured to interact with the negative-pressure pathway so that the collapsible conduit collapses along its length upon application of negative pressure to the negative-pressure pathway. In some embodiments, the instillation pathway comprises no internal support. In some embodiments, the negative-pressure pathway and/or instillation pathway may be configured to fluidly communicate with the ambient environment through the aperture, for example allowing instillation fluid and/or negative pressure to be applied to a tissue site. In some embodiments, the instillation pathway may be configured to interact with the plurality of supports of the negative-pressure pathway to maintain an open pathway for instillation when the instillation pathway is under compression.

In some embodiments, the plurality of supports may be co-extensive with the negative-pressure pathway. The instillation pathway and the negative-pressure pathway may be located within a single bridge, in some embodiments. For example, the instillation pathway may be located within the negative-pressure pathway and may extend lengthwise substantially for the length of the negative-pressure pathway. In some embodiments, the plurality of supports may be formed in one or more spacer layers. For example, the negative-pressure pathway may comprise two spacer layers, each having supports extending inward into the enclosed space of the negative-pressure pathway, and the instillation pathway may be located between the spacer layers. In some embodiments, the apparatus may be configured with a low profile.

In some embodiments, the negative-pressure pathway may comprise a first layer, which can be coupled to the instillation pathway to form the enclosed space of the negative-pressure pathway. For example, the first layer may be sealed about a perimeter to the instillation pathway, so that the instillation pathway and the first layer jointly form the enclosed space of the negative-pressure pathway. In some embodiments, the supports may be located in the enclosed space of the negative-pressure pathway, between the first layer and the instillation pathway. For example, the supports may extend from the first layer towards and/or contacting the instillation pathway. In some embodiments, the instillation pathway may be in stacked relationship with the negative-pressure pathway.

In some embodiments, the instillation pathway may be located in a separate bridge from the negative-pressure pathway. The instillation pathway may comprise a plurality of instillation supports configured to support the instillation pathway, and a gap between the plurality of supports configured to allow collapse across the width of the instillation pathway upon application of negative pressure. For example, the gap may not include any instillation supports. In some embodiments, the plurality of instillation supports may be co-extensive with the instillation pathway, except for the gap.

Some embodiments may relate to an apparatus for distributing liquid to a tissue site, and the apparatus may comprise an instillation pathway that is pneumatically isolated from the ambient environment except through an instillation aperture in a distal end; a plurality of instillation supports within the instillation pathway configured to support the instillation pathway; and a gap between the plurality of supports configured to allow collapse across the width of the instillation pathway upon application of negative pressure. In some embodiments, the gap may not have any instillation supports; and collapse of the instillation pathway may be sufficient to close the instillation pathway, substantially preventing fluid flow through the instillation pathway. The plurality of instillation supports may be co-extensive with the instillation pathway, except for the gap. In some embodiments, the apparatus may be configured with a low profile. For example, the apparatus may be an instillation bridge.

A system for distributing negative pressure and instillation fluid to a tissue site is also described herein, wherein some example embodiments include a negative-pressure pathway; an instillation pathway that is pneumatically isolated from the ambient environment and from the negative-pressure pathway except through an instillation aperture in a distal end; a plurality of instillation supports within the instillation pathway that are configured to support the instillation pathway; and a gap between the plurality of instillation supports configured to allow collapse across the width of the instillation pathway upon application of negative pressure. Typically, the instillation pathway may be configured to interact with the negative-pressure pathway so that, upon application of negative pressure to the negative-pressure pathway, the gap collapses. For example, collapse of the instillation pathway may be sufficient to close the instillation pathway, substantially preventing fluid flow through the instillation pathway. In some embodiments, the plurality of instillation supports may be co-extensive with the instillation pathway, except for the gap. In some embodiments, the plurality of instillation supports may be arranged in rows, with the rows aligned. The instillation pathway may be located in a separate bridge from the negative-pressure pathway, in some embodiments. For example, each of the instillation pathway bridge and the negative-pressure pathway bridge may be configured with a low profile.

Still other exemplary embodiments relate to an apparatus for managing fluid at a tissue site, and the apparatus may comprise a negative-pressure pathway; and an instillation pathway configured to maintain an open fluid pathway when fluid is applied therethrough, and configured to interact with the negative-pressure pathway so that, upon application of negative pressure to the negative-pressure pathway, at least a portion of the instillation pathway collapses. In some embodiments, the instillation pathway is pneumatically isolated from the ambient environment and from the negative-pressure pathway except through an aperture in a distal end. Collapse of at least a portion of the instillation pathway may be sufficient to close the instillation pathway, substantially preventing fluid flow through the instillation pathway.

In some embodiments, the instillation pathway may be located in a separate bridge from the negative-pressure pathway. The instillation pathway may comprise a plurality of instillation supports configured to support the instillation pathway, and a gap between the plurality of instillation supports configured to allow collapse across the width of the instillation pathway upon application of negative pressure. For example, except for the unsupported gap, the plurality of instillation supports may be fully co-extensive with the instillation pathway.

In some embodiments, the instillation pathway and the negative-pressure pathway may both be located in a single bridge. The negative-pressure pathway may comprise a plurality of supports configured to support the negative-pressure pathway to prevent the negative-pressure pathway from collapsing. In some embodiments, the instillation pathway may be located within the negative-pressure pathway. The instillation pathway may comprise a collapsible conduit configured to be collapsible along its entire length. For example, the instillation pathway may have no internal support.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 15A is a plan view of the bridge of FIG. 14;

FIG. 15B is a schematic longitudinal cross-section slice view of the bridge of FIG. 15A;

FIG. 18A is a plan view of the instillation bridge of FIG. 17;

FIG. 18B is a schematic longitudinal cross-section slice view of the instillation bridge of FIG. 18A;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
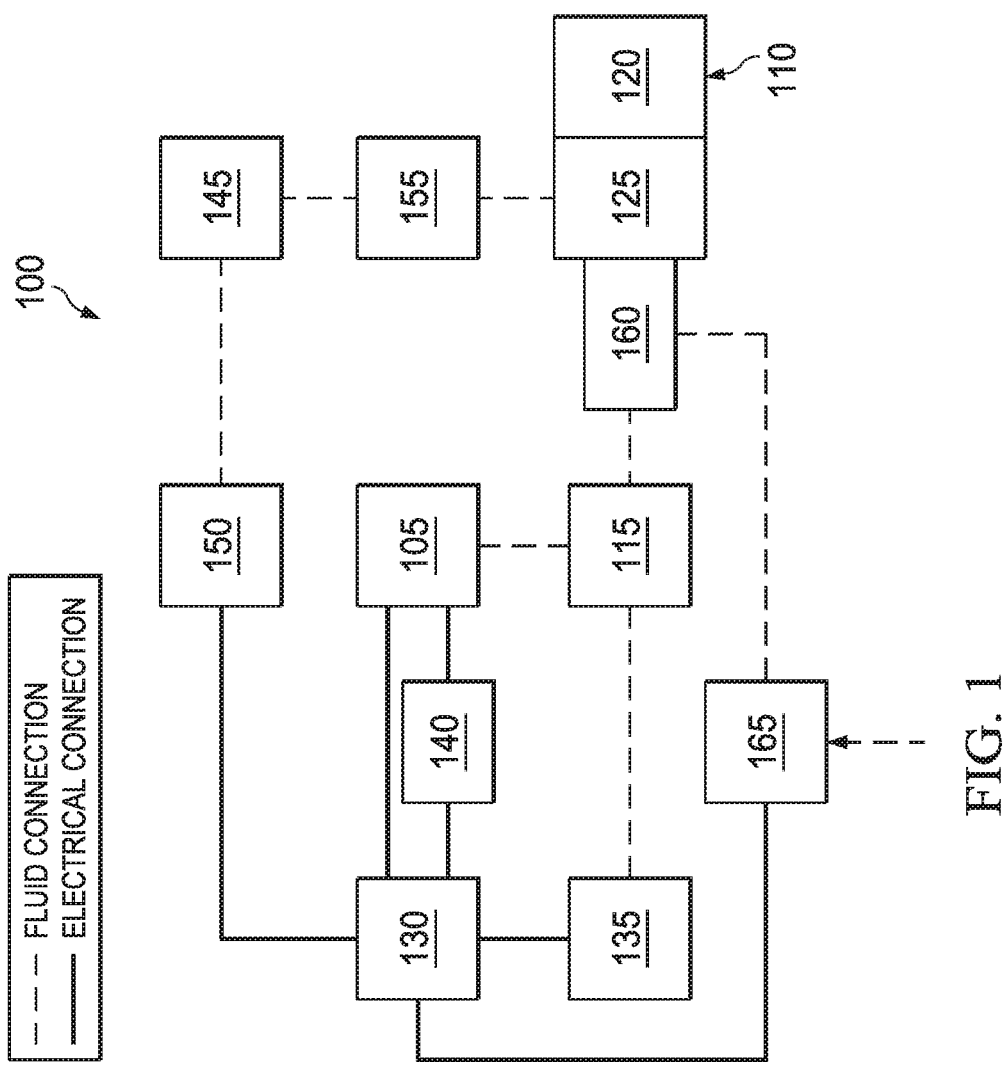
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. A tube, for example, is generally an elongated, flexible structure with a cylindrical lumen, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSAT.R.A.C.™ Pad, available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source, such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

In some examples, a bridge 160 may fluidly couple the dressing 110 to the negative-pressure source 105, as illustrated in FIG. 1. The therapy system 100 may also comprise a flow regulator, such as a regulator 165, fluidly coupled to a source of ambient air to provide a controlled or managed flow of ambient air. In some embodiments, the regulator 165 may be fluidly coupled to the tissue interface 120 through the bridge 160. In some embodiments, the regulator 165 may be positioned proximate to the container 115 and/or proximate a source of ambient air, where the regulator 165 is less likely to be blocked during usage.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols, such as polyester or polyether, isocyanate, such as toluene diisocyanate, and polymerization modifiers, such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment. In some embodiments, the regulator 165 may control the flow of ambient air to purge fluids and exudates from the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure.

Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. In some examples, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative pressure from ambient pressure to the target pressure may not be instantaneous. For example, the negative-pressure source 105 and the dressing 110 may have an initial rise time, which can vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In other examples, a target pressure can vary with time in a dynamic pressure mode. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 2:
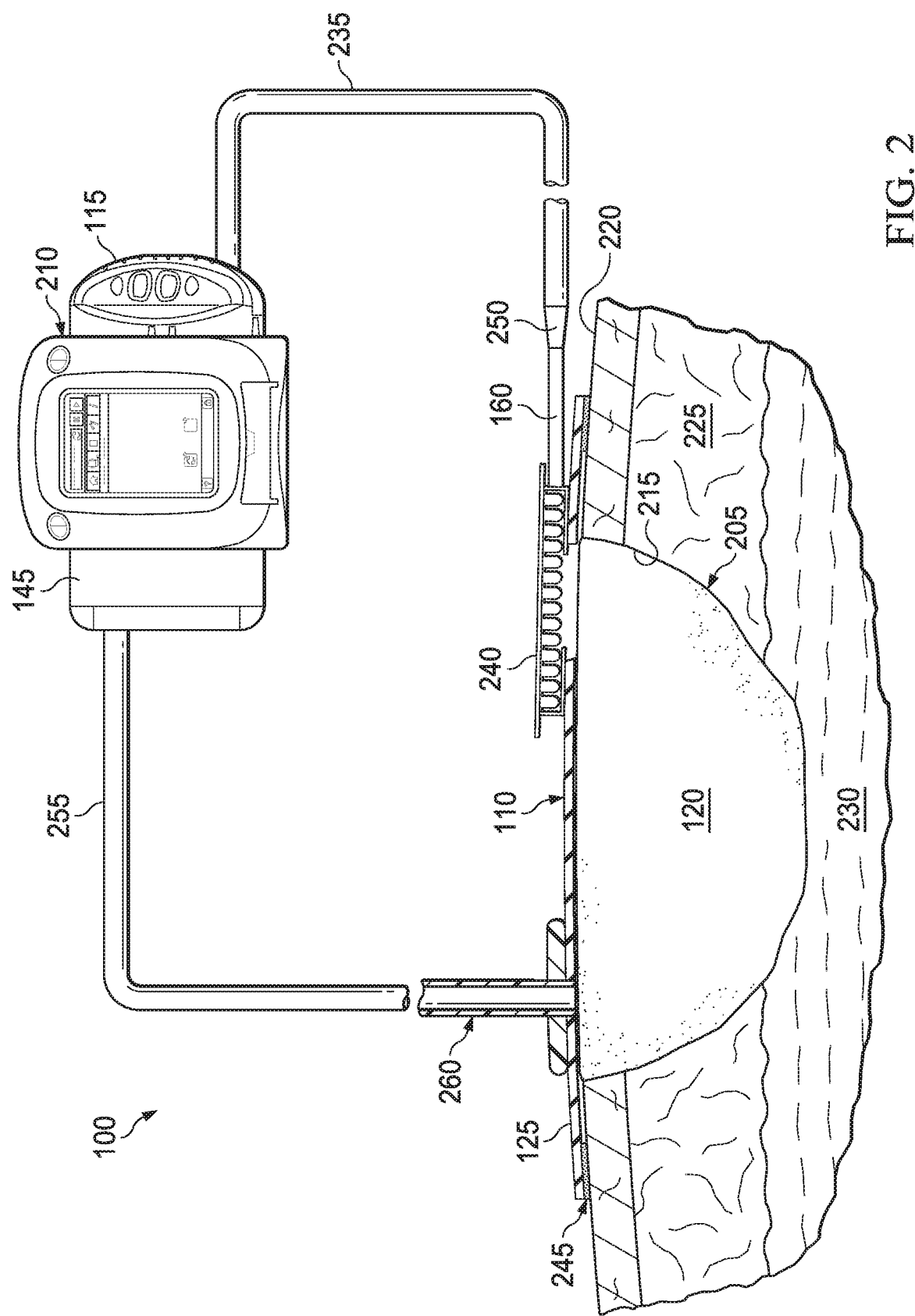
FIG. 2 is a schematic diagram of an example embodiment of the therapy system of FIG. 1 configured to apply negative pressure and treatment solutions to a tissue site.

FIG. 2 is a schematic diagram of an example embodiment of the therapy system 100 configured to apply negative pressure and treatment solutions to a tissue site 205. Some components of the therapy system 100 may be housed within or used in conjunction with other components, such as processing units, alarm indicators, memory, databases, software, display devices, or user interfaces that further facilitate therapy. For example, in some embodiments, the negative-pressure source 105 may be combined with the controller 130 and other components into a therapy unit, such as a therapy unit 210 illustrated in FIG. 2. The therapy unit 210 may be, for example, a V.A.C.ULTA™ Therapy Unit available from Kinetic Concepts, Inc. of San Antonio, Texas.

In the example of FIG. 2, the tissue site 205 is at least partially defined by a wound edge 215, which extends through an epidermal layer 220 and a dermal layer 225 and reaches into a hypodermis, or subcutaneous tissue 230. The therapy system 100 may be used to treat a wound of any depth, as well as many different types of wounds, including open wounds, incisions, or other tissue sites. Treatment of the tissue site 205 may include removal of fluids originating from the tissue site 205, such as exudates or ascites, or fluids instilled into the dressing to cleanse or treat the tissue site 205, such as antimicrobial solutions.

In the example of FIG. 2, a conduit 235 fluidly couples the container 115 to another fluid conductor, such as the bridge 160, which provides a fluid pathway between the conduit 235 and the tissue interface 120. The bridge 160 in the example of FIG. 2 is a substantially flat and flexible fluid conductor, but can also be compressed without occluding or blocking the fluid pathway between the conduit 235 and the tissue interface 120. In some embodiments, the bridge 160 may comprise or be coupled to an applicator 240 adapted to be positioned in fluid communication with the tissue interface 120 through an aperture in the cover 125. The cover 125 may be sealed to the epidermal layer 220 with an attachment device, such as an adhesive layer 245.

In some embodiments, the applicator 240 may be integral to the bridge 160. In other embodiments, the applicator 240 and the bridge 160 may be separate components that are coupled together to form a single device. In yet other embodiments, the applicator 240 and the bridge 160 may be separate components that may be used independently of each other in the therapy system 100.

The bridge 160 may have a substantially flat profile, and an adapter 250 may be configured to fluidly couple the bridge 160 to a tube or other round fluid conductor, such as the conduit 235 illustrated in the example of FIG. 2. In some embodiments, the adapter 250 may have one or more sealing valves, which can isolate the conduit 235 if separated from the bridge 160.

The example of FIG. 2 also illustrates a configuration of the therapy system 100 in which the solution source 145 is fluidly coupled to the tissue interface 120 through a conduit 255 and a dressing interface 260.

Figure 3A:
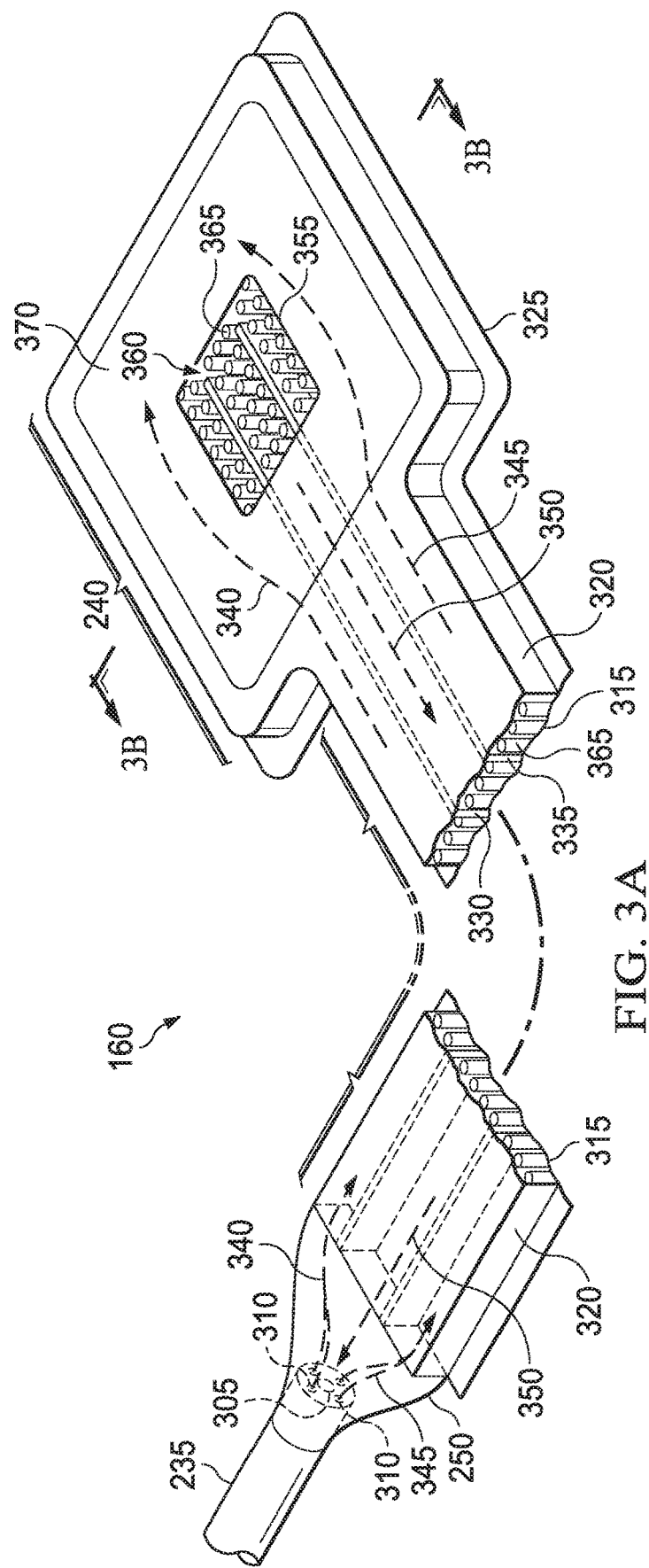
FIG. 3A is a segmented perspective bottom view of an example of a bridge that may be associated with some embodiments of the therapy system of FIG. 1.

FIG. 3A is a segmented perspective bottom view of an example of the bridge 160, illustrating additional details that may be associated with some embodiments. The bridge 160 of FIG. 3A generally has a low profile structure. FIG. 3A further illustrates features that may be associated with some embodiments of the applicator 240 of FIG. 2. The applicator 240 may be bulbous or any shape suitable for facilitating a connection to the dressing 110. The bridge 160 in the example of FIG. 3A is generally long and narrow. An adapter, such as the adapter 250, may fluidly couple the bridge 160 to a fluid conductor, such as the conduit 235. In some examples, the conduit 235 may be a multi-lumen tube in which a central lumen 305 is configured to couple the bridge 160 to a negative-pressure source, and one or more peripheral lumens 310 are configured to couple the bridge 160 to a sensor, such as the first sensor 135.

In some embodiments, the bridge 160 may comprise a liquid barrier formed from two layers. In FIG. 3A, for example, a periphery of a first layer 315 may be coupled to a second layer 320 to form a fluid path between two ends of the bridge 160, including the applicator 240. The first layer 315 and the second layer 320 may both be formed from or include a polymeric film of liquid-impermeable material. In some examples, the first layer 315, the second layer 320, or both may be formed from the same material as the cover 125. The first layer 315 and the second layer 320 may be coupled around the periphery of the bridge 160 to form the sealed space by welding (RF or ultrasonic), heat sealing, or adhesive bonding, such as acrylics or cured adhesives. For example, the first layer 315 and the second layer 320 may be welded together around the periphery of the bridge 160 and may form a flange 325 around the periphery of the bridge 160 as a result of the weld.

The bridge 160 of FIG. 3A may further comprise at least one barrier or wall, such as a first wall 330, between the first layer 315 and the second layer 320. In some embodiments, the first wall 330 may extend from the end of the bridge 160 adjacent to the adapter 250 into the applicator 240 to form at least two sealed spaces or fluid pathways between the first layer 315 and the second layer 320 within the bridge 160. In some examples, the bridge 160 may further comprise a second barrier, such as a second wall 335, between the first layer 315 and the second layer 320. In some embodiments, the second wall 335 also may extend from the end of the bridge 160 adjacent to the adapter 250 into the applicator 240. In some example embodiments, the first wall 330 and the second wall 335 may comprise a polymeric film coupled to the first layer 315 and the second layer 320. In some other example embodiments, the first wall 330 and the second wall 335 may comprise a weld (RF or ultrasonic), a heat seal, an adhesive bond, or a combination of any of the foregoing. In some embodiments, the first wall 330 and the second wall 335 may form distinct fluid pathways within the sealed space between the first layer 315 and the second layer 320. In FIG. 3A, for example, the first wall 330 and the second wall 335 define in part a first pathway 340, a second pathway 345, and a third pathway 350. Each of the first pathway 340, the second pathway 345, and the third pathway 350 generally has a first end, a second end, and a longitudinal axis. In some embodiments, one or more of the fluid pathways may be fluidly coupled or configured to be fluidly coupled to the peripheral lumens 310, which can provide a pressure feedback path to a sensor, such as the first sensor 135. The third pathway 350 may be fluidly coupled to or configured to be fluidly coupled to the central lumen 305.

In some example embodiments, the first pathway 340, the second pathway 345, and the third pathway 350 may be fluidly coupled to the conduit 235 through the adapter 250. For example, the third pathway 350 may be fluidly coupled to the conduit 235 so that the third pathway 350 can deliver negative pressure to the tissue interface 120. Each of the first pathway 340 and the second pathway 345 may be fluidly coupled to a separate one of the peripheral lumens 310. In other embodiments, the first pathway 340 and the second pathway 345 both may be fluidly coupled to a common space within the adapter 250, which can be fluidly coupled to one or more of the peripheral lumens 310. In some example embodiments, the first pathway 340, the second pathway 345, and the third pathway 350 may terminate within the applicator 240. In some embodiments, the first pathway 340, the second pathway 345, and the third pathway 350 may be in fluid communication with each other within the applicator 240 for delivering and sensing negative pressure associated with the tissue interface 120.

The bridge 160 may comprise an opening or aperture, such as an aperture 355, adapted to fluidly couple the sealed space of the bridge 160 to the tissue interface 120. In FIG. 3A, for example, the aperture 355 is disposed in the applicator 240. A recessed space 360 within the bridge 160 can be adapted to be in fluid communication with the tissue interface 120 through the aperture 355 in use. In the example of FIG. 3A, the portions of first layer 315 and the second layer 320 at least partially define the recessed space 360 within the sealed space of the applicator 240. In some example embodiments, the first wall 330 and the second wall 335 may extend only partially into the recessed space 360 so that the ends of the first wall 330 and the second wall 335 are exposed by the aperture 355 as shown in the example of FIG. 3A. In some embodiments, the first pathway 340 and the second pathway 345 may be in fluid communication with the recessed space 360. The third pathway 350 may also be in fluid communication with the recessed space 360 and can be adapted to deliver negative pressure to the tissue interface 120 through the recessed space 360. In some example embodiments (not shown), the first wall 330 and the second wall 335 may extend beyond the aperture 355 so that less of the first pathway 340 and the second pathway 345 are exposed to negative pressure delivered to the tissue interface 120 to prevent or reduce occlusions and/or blockages.

The bridge 160 may further comprise a means for supporting fluid paths under pressure. In some embodiments, the means of support may comprise a plurality of support features, such as a flexible projections, standoffs, nodes, cells, porous textile, porous foam, or some combination of features disposed in a fluid path. For example, the bridge 160 of FIG. 3A comprises a plurality of supports 365. Adjacent to the aperture 355, the supports 365 may be adapted to come in direct contact with the tissue interface 120 in some examples. Support features such as the supports 365 can provide a cushion to prevent the sealed spaces of the bridge 160 from collapsing as a result of external forces. In some example embodiments, the supports 365 may come in contact with the second layer 320, and in some other example embodiments, the top portion of the supports 365 may be coupled to the second layer 320. In some example embodiments, the supports 365 may be disposed only in the applicator 240, and other support features may be disposed in the bridge 160 between the applicator 240 and the conduit 235.

The bridge 160 of FIG. 3A may also comprise an affixation surface 370 surrounding the aperture 355, which can be coupled to the dressing 110 or directly to a tissue site in some examples. In some embodiments, a top drape (not shown) may be utilized to cover the applicator 240 for additional protection and support over the applicator 240 if applied to a tissue site. In some embodiments, a top drape may also be utilized to cover any adhesive that might be exposed. In some embodiments, a top drape may be similar to the cover 125. For example, a top drape may comprise or consist essentially of a polymer, such as a polyurethane film.

Figure 3B:
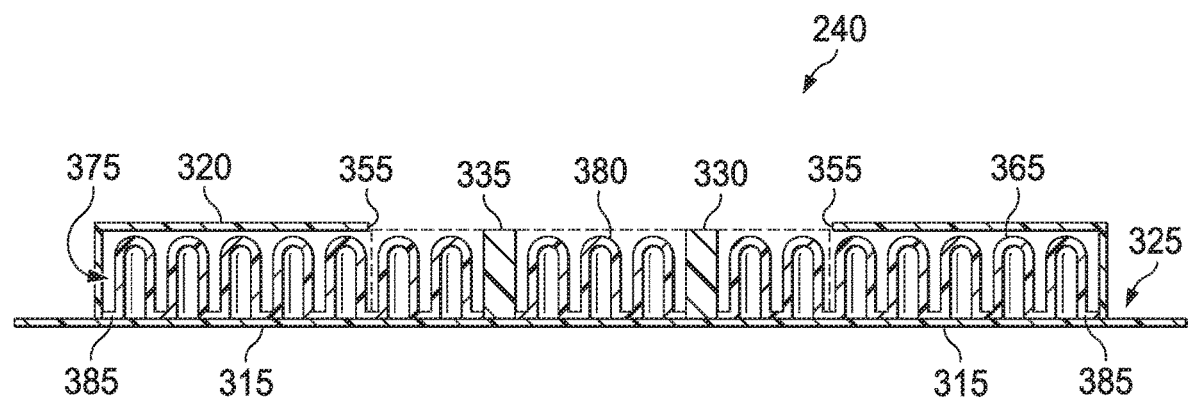
FIG. 3B is a schematic view of an applicator that may be associated with some embodiments of the bridge of FIG. 3A.

FIG. 3B is a schematic view of the applicator 240 of FIG. 3A, taken along line 3B-3B, illustrating additional details that may be associated with some embodiments. For example, some embodiments of the support features may be formed by sealing a spacer layer 375 to the first layer 315. In the example of FIG. 3B, each of the supports 365 comprises a standoff 380 in the spacer layer 375. In some embodiments, the standoffs 380 may be formed by blisters, bubbles, cells or other raised formations that extend above or below a base 385 of the spacer layer 375, for example. In some examples, the standoffs 380 may be vacuum-formed regions of the spacer layer 375.

The base 385 may be sealed to the first layer 315, and the standoffs 380 may extend from the first layer 315 toward the aperture 355 of the second layer 320 as illustrated in FIG. 3B. At least some of the supports 365 may be configured to come in direct contact with the tissue interface 120 through the aperture 355.

In some embodiments, the base 385 may be sealed to the first layer 315 so that the first layer 315 closes the standoffs 380. For example, the base 385 may be heat-sealed to the first layer 315 while the standoffs 380 may be vacuum-formed simultaneously. In other examples, the seal may be formed by adhesion between the first layer 315 and the spacer layer 375. Alternatively, the first layer 315 and the spacer layer 375 may be adhesively bonded to each other.

In general, the supports 365 are structured so that they do not completely collapse from apposition forces resulting from the application of negative pressure and/or external forces to the bridge 160. In some examples, the first layer 315 and the spacer layer 375 may be formed from separate sheets or film brought into superposition and sealed, or they may be formed by folding a single sheet onto itself with a heat-sealable surface facing inward. Any one or more of the first layer 315, second layer 320, and the spacer layer 375 also may be a monolayer or multilayer structure, depending on the application or the desired structure of the support features.

In some example embodiments, the standoffs 380 may be substantially airtight to inhibit collapsing of the standoffs 380 under negative pressure, which could block the flow of fluid through the bridge 160. For example, in the embodiment of FIG. 3B, the standoffs 380 may be substantially airtight and have an internal pressure that is an ambient pressure. In another example embodiment, the standoffs 380 may be inflated with air or other suitable gases, such as carbon dioxide or nitrogen. The standoffs 380 may be inflated to have an internal pressure greater than the atmospheric pressure to maintain their shape and resistance to collapsing under pressure and external forces. For example, the standoffs 380 may be inflated to a pressure up to about 25 psi above the atmospheric pressure.

In some embodiments, the first layer 315, the second layer 320, and the spacer layer 375 may each have a thickness within a range of 400 to 600 microns. For example, the first layer 315, the second layer 320, and the spacer layer 375 may be formed from thermoplastic polyurethane film having a thickness of about 500 microns. In some example embodiments, each may have a thickness of about 200 µm to about 600 µm. In some embodiments, a thickness of about 500 µm or about 250 µm may be suitable.

In some embodiments, one or more of the first layer 315, the second layer 320, and the spacer layer 375 may have a different thickness. For example, the thickness of the second layer 320 may be up to 50% thinner than the thickness of the spacer layer 375. If the fabrication process comprises injection molding, portions of the spacer layer 375 defining the standoffs 380 may have a thickness between about 400 µm and about 500 µm. However, if the standoffs 380 are fabricated by drawing a film, the spacer layer 375 proximate a top portion of the standoffs 380 may have a thickness as thin as 50 µm.

After the standoffs 380 have been fabricated, the walls of the standoffs 380 may have a thickness relative to the thickness of base 385. The relative thickness may be defined by a draw ratio, such as the ratio of the average height of the standoffs 380 to the average thickness of the spacer layer 375. In some example embodiments, the standoffs 380 may have a generally tubular shape, which may have been formed from the spacer layer 375 having various thicknesses and draw ratios. In some example embodiments, the spacer layer 375 may have an average thickness of 500 µm and the standoffs 380 may have an average height in a range between about 2.0 mm and 5.0 mm. Consequently, the standoffs 380 may have a draw ratio ranging from about 4:1 to about 10:1 for heights of 2.0 and 5.0 mm, respectively. In another example embodiment, the draw ratio may range from about 5:1 to about 13:1 where the thickness of the spacer layer 375 is an average of about 400 µm. In yet other example embodiments, the draw ratio may range from about 3:1 to about 9:1 where the thickness of the spacer layer 375 is an average of about 600 µm. In some embodiments, the standoffs 380 may have an average height in a range between about 1.0 mm and 4.0 mm, depending on the thickness of the spacer layer 375. The spacer layer 375 may have varying thicknesses and flexibilities, but is substantially non-stretchable so that the standoffs 380 maintain a generally constant volume if sealed to the first layer 315. Additionally, the standoffs 380 can support a load without bursting and can recover their original shape after a load is removed.

In some example embodiments, any one or more of the first layer 315, the second layer 320, and the spacer layer 375 may be formed from a non-porous, polymeric film that may comprise any flexible material that can be manipulated to form suitable support features, including various thermoplastic materials, e.g., polyethylene homopolymer or copolymer, polypropylene homopolymer or copolymer, etc. Non-limiting examples of suitable thermoplastic polymers may include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials may also be suitable, such as polypropylene homopolymer or polypropylene copolymer (e.g., propylene/ethylene copolymer), polyesters, polystyrenes, polyamides, polycarbonates, etc.

In some embodiments, the polymeric film may possess sufficient tensile strength to resist stretching under apposition forces created by negative-pressure therapy. The tensile strength of a material is the ability of material to resist stretching as represented by a stress-strain curve where stress is the force per unit area, i.e., pascals (Pa), newtons per square meter ($N/m^2$), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high density polyethylene (HDPE) has a high tensile strength and low-density polyethylene (LDPE) has a slightly lower tensile strength, which are suitable materials for the sheets of non-porous, polymeric film as set forth above. Linear low density polyethylene (LLDPE) may also be suitable for some examples because the material stretches very little as the force is increased up to the yield point of the material. Thus, the standoffs 380 or other support features can be configured to resist collapsing (or stretching) when subjected to an external force or pressure. For example, HDPE has a UTS of about 37 MPa and may have a yield strength that ranges from about 26-33 MPa depending on the thickness of the material, while LDPE has somewhat lower values.

In some example embodiments, one or more of the first layer 315, the second layer 320, and the spacer layer 375 may comprise or consist essentially of a thermoplastic polyurethane (TPU) film that is permeable to water vapor but impermeable to liquid. The film may be in various degrees breathable and may have MVTRs that are proportional to their thickness. For example, the MVTR may be at least 300 $g/m^2$ per twenty-four hours in some embodiments. For permeable materials, the permeability generally should be low enough to maintain a desired negative pressure for the desired negative-pressure treatment.

In some example embodiments, the thermoplastic polyurethane film may be, for example, a Platilon® thermoplastic polyurethane film available from Convestro LLC, which may have a UTS of about 60 MPa and may have a yield strength of approximately 11 MPa or greater than about 10 MPa depending on the thickness of the material. Therefore, in some example embodiments, it is desirable that the non-porous, polymeric film may have a yield strength greater than about 10 MPa, depending on the type and thickness of material. A material having a lower yield strength may be too stretchable and, therefore, more susceptible to breaking with the application of small amounts of compression and/or apposition forces.

Figure 3C:
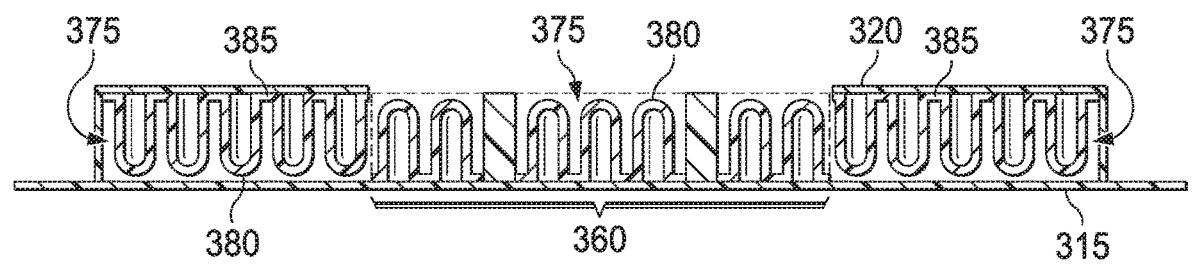
FIG. 3C is a schematic view of another example of an applicator that may be associated with some embodiments of the bridge of FIG. 3A.

FIG. 3C is a schematic view of another example of the applicator 240, illustrating details that may be associated with some embodiments. In the example of FIG. 3C, the applicator 240 has more than one spacer layer 375. At least some of the support features may be formed by sealing the base 385 of at least one of the spacer layers 375 to the second layer 320. Some of the supports 365 may extend from the second layer 320 toward the first layer 315 around the recessed space 360. In the example of FIG. 3C, all of the supports 365 around the recessed space 360 extend from the second layer 320 toward the first layer 315. At least some of the supports 365 may also extend from the first layer 315 toward the aperture 355 in the recessed space 360.

Figure 3D:
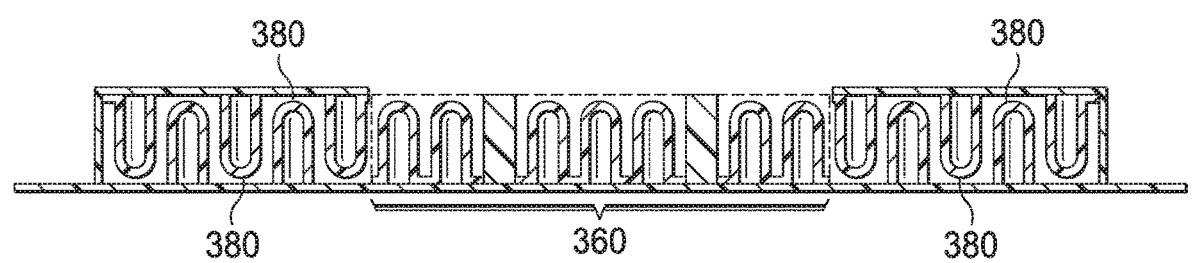
FIG. 3D is a schematic view of another example of an applicator that may be associated with some embodiments of the bridge of FIG. 3A.

FIG. 3D is a schematic view of another example of the applicator 240, illustrating additional details that may be associated with some embodiments. In the example of FIG. 3D, some of the supports 365 around the recessed space 360 extend from the second layer 320 toward the first layer 315, and some of the supports 365 around the recessed space 360 also extend from the first layer 315 toward the second layer 320. Some of the supports 365 also extend from the first layer 315 toward the aperture 355 in the recessed space 360.

Figure 4A:
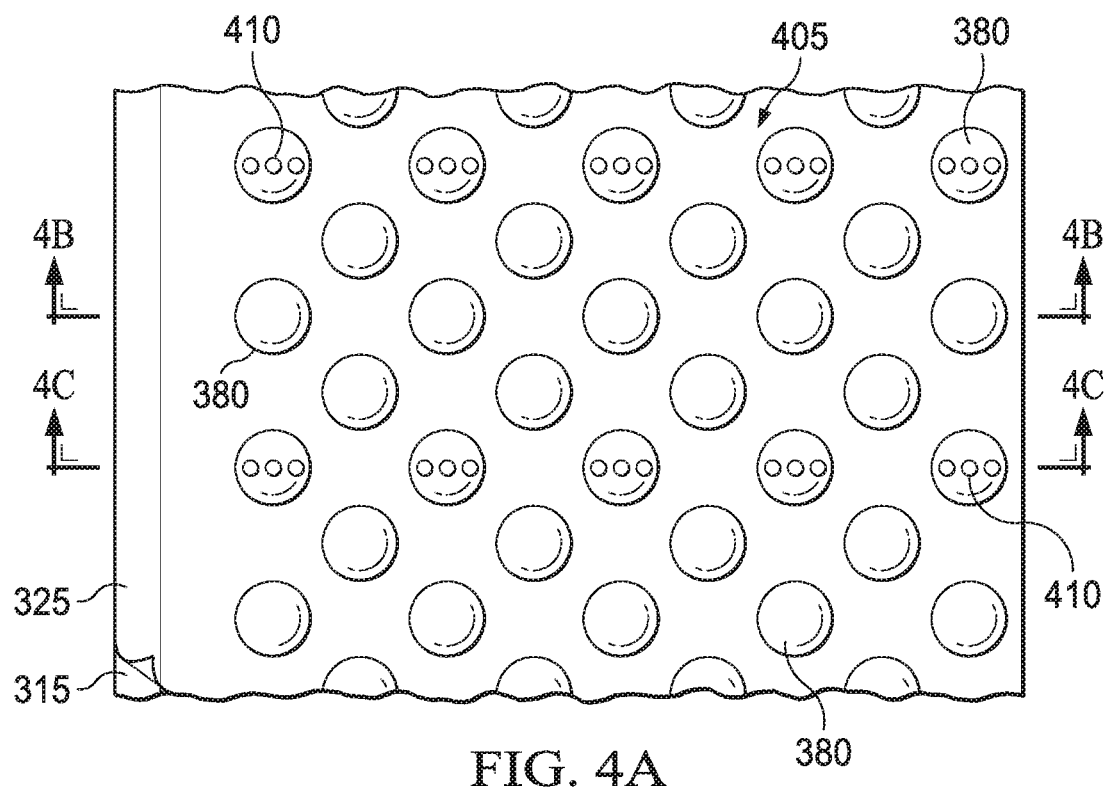
FIG. 4A is a schematic view of additional details that may be associated with various examples of support features in a bridge.

FIG. 4A is a schematic view of additional details that may be associated with various examples of support features in the bridge 160. For example, FIG. 4A illustrates a sealed region 405 between the standoffs 380. In some embodiments, the sealed region 405 may be formed by sealing portions of the spacer layer 375 to the first layer 315 or the second layer 320. In the example of FIG. 4A, the sealed region 405 may be formed by sealing the base 385 to the first layer 315 around the standoffs 380. As illustrated in the example of FIG. 4A, the standoffs 380 may have a circular edge proximate to the sealed region 405. In other embodiments, the standoffs 380 may have edges with other suitable shapes, such as rectangular, triangular, or hexagonal, or some combination of shapes. Additionally or alternatively, one or more of the standoffs 380 may be embossed with projections or nodes, such as the nodes 410 illustrated in the example of FIG. 4A.

The standoffs 380 in adjacent rows or columns may be staggered so that the standoffs 380 may be nested or packed together, as illustrated in the example of FIG. 4A. In other embodiments, the standoffs 380 may be arranged in other patterns suitable for the particular therapy being utilized. For example, the rows and columns of the standoffs 380 may be arranged in line to form an aligned, rectangular pattern so that there is more spacing between the standoffs 380. Increasing the spacing between the standoffs 380 may increase fluid flow within the fluid pathways of the bridge 160, whereas a nested arrangement may restrict fluid flow within the fluid pathways. For example, the standoffs 380 can be aligned to increase fluid flow of negative pressure being applied to a tissue interface and facilitate the removal of fluids and exudates within the recessed space 360. A nested pattern can facilitate pressure sensing within the recessed space 360 while impeding the inflow of fluids and exudates, which can reduce the possibility of blockage.

In some embodiments, distribution of the standoffs 380 may be characterized by a pitch, which can be defined by the center to center distance between each of the standoffs 380. For example, a pitch of about 1 mm to about 10 mm may be suitable for some configurations. In some embodiments, the pitch may be between about 2 mm and about 3 mm. Because the sealed region 405 can define an end of the standoffs 380, including a diameter of a circular end, and the pitch of the standoffs 380, the area of the spacer layer 375 having the standoffs 380 may also be determined as a percentage. For example, if each of the standoffs 380 has a diameter of about 1.0 mm and the pitch is about 2.0 mm, the coverage percentage is about 22% of the area of the spacer layer 375. In another example, if the diameter of each of the standoffs 380 is about 2.0 mm and the pitch is about 5.0 mm, the coverage percentage is about 14% of the area of the spacer layer 375. In yet another example, if the diameter of each of the standoffs 380 is about 1.5 mm, the pitch is about 2.0 mm, and the standoffs 380 are more tightly arranged such that there are about 28.5 standoffs in a 10 mm² section of the spacer layer 375, the coverage percentage is about 51% of the area of the spacer layer 375. Depending on the diameter, pitch, and arrangement of the standoffs 380, the coverage percentage may range between about 10% and about 60% of the surface area of the spacer layer 375. Support features having other shapes also may have a coverage percentage in generally the same range.

The size and pitch of the standoffs 380 also may be varied to effect change in the fluid flows through the fluid passageways. For example, the diameter and pitch of the standoffs 380 can be increased to increase fluid flow of negative pressure being applied to a tissue interface and facilitate the removal of fluids and exudates within the recessed space 360. The diameter, pitch, or both may be decreased to restrict fluid flow, which can reduce blockages, and facilitate pressure sensing within the recessed space 360.

Figure 4B:
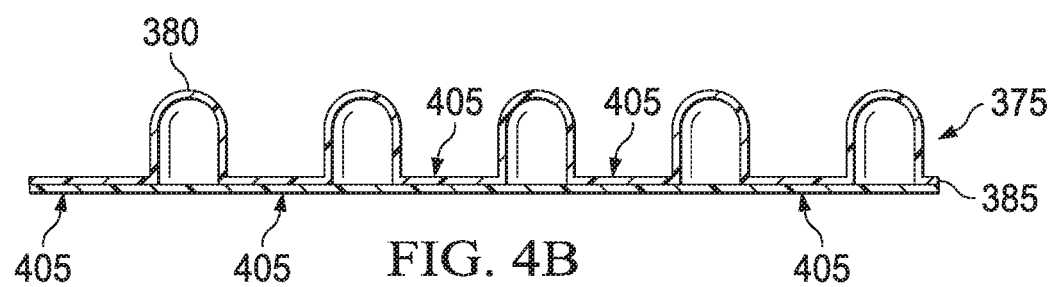
FIG. 4B is a schematic view of the support features of FIG. 4A taken along section 4B-4B, illustrating additional details that may be associated with some examples.

FIG. 4B is a schematic view of the support features of FIG. 4A taken along section 4B-4B, illustrating additional details that may be associated with some examples. In some embodiments, the standoffs 380 may have a hemispherical profile, as illustrated in the example of FIG. 4B. In other example embodiments, the standoffs 380 may be profiles that are conical, cylindrical, tubular having a flattened or hemispherical end, or geodesic. The standoffs 380 may be tubular in some embodiments, formed with generally parallel walls extending from the base 385 to a hemispherical or flat top portion of the standoffs 380. Alternatively, the walls of the standoffs 380 may taper or expand outwardly from the base 385. In some embodiments, the standoffs 380 that are generally hemispherical or tubular in shape may have a diameter between about 1.0 mm and about 10 mm. In some other embodiments, the standoffs 380 may have a diameter between about 2.0 mm and about 5.0 mm.

Figure 4C:
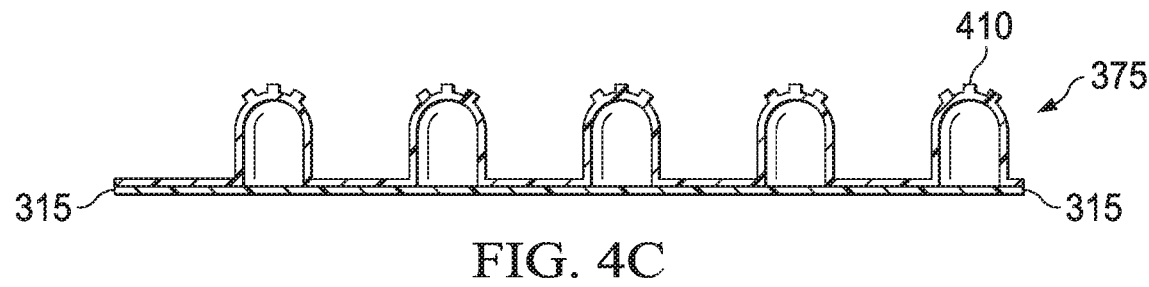
FIG. 4C is a schematic view of the example support features of FIG. 4A taken along section 4C-4C, illustrating additional details that may be associated with some embodiments.

FIG. 4C is a schematic view of the example support features of FIG. 4A taken along section 4C-4C, illustrating additional details that may be associated with some embodiments. In the example of FIG. 4C, the nodes 410 can be configured to contact the tissue interface 120 to enhance fluid flow to a tissue site. The nodes 410 may be flexible or rigid. In some embodiments, the nodes 410 may be formed from a substantially gas impermeable material, such as silicone. In other embodiments, the nodes 410 may be formed from a semi-gas permeable material. The nodes 410 may be formed from the same material as the spacer layer 375, and may be an integral part of the spacer layer 375. In some embodiments, the nodes 410 may be solid, while in other embodiments the projections may be hollow to increase flexibility. The nodes 410 may form a plurality of channels and/or voids to distribute reduced pressure and allow for fluid flow among the nodes 410. The nodes may be dimensioned to provide local load points evenly distributed at a tissue interface. The pattern and position of the nodes 410 may be uniform or non-uniform. The nodes may have different profiles, including, for example, the shape of a spike, cone, pyramid, dome, cylinder or rectangle.

Figure 5A:
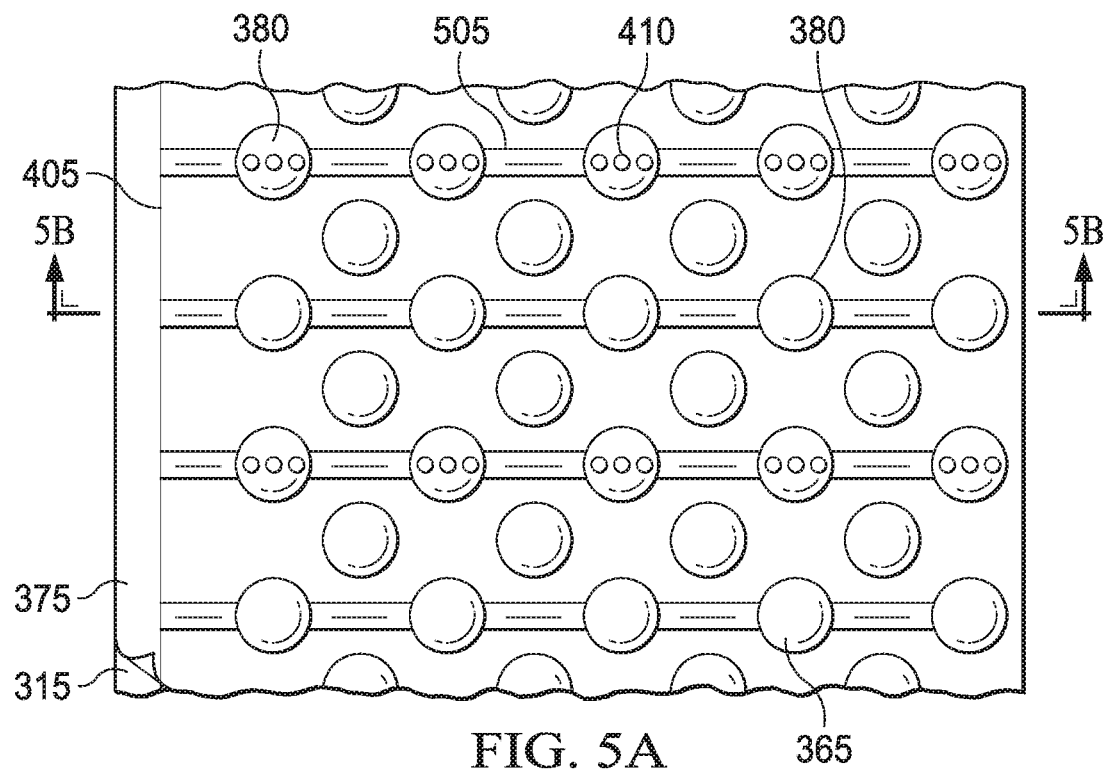
FIG. 5A is a schematic view of additional details that may be associated with some embodiments of a bridge in the therapy system of FIG. 1.

FIG. 5A is a schematic view of additional details that may be associated with some embodiments of the bridge 160. For example, in FIG. 5A one or more passageways 505 may be formed between the supports 365.

Figure 5B:
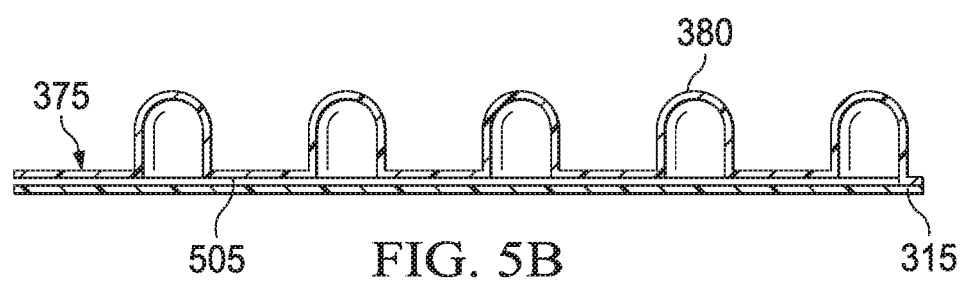
FIG. 5B is a schematic view taken along section 5B-5B of FIG. 5A, illustrating additional details that may be associated with some embodiments.

FIG. 5B is a schematic view taken along section 5B-5B of FIG. 5A, illustrating additional details that may be associated with some embodiments. For example, as seen in FIG. 5B, at least some of the standoffs 380 may be fluidly coupled through the passageways 505. The passageways 505 and the standoffs 380 can form a closed chamber. In some examples, a closed chamber may be formed by all of the standoffs 380 in a row fluidly coupled by the passageways 505 as shown in FIG. 5A and FIG. 5B. The closed chambers may be formed in alternating rows as also shown in FIG. 5A. The formation of closed chambers with the standoffs 380 can distribute apposition forces more equally.

Figure 6A:
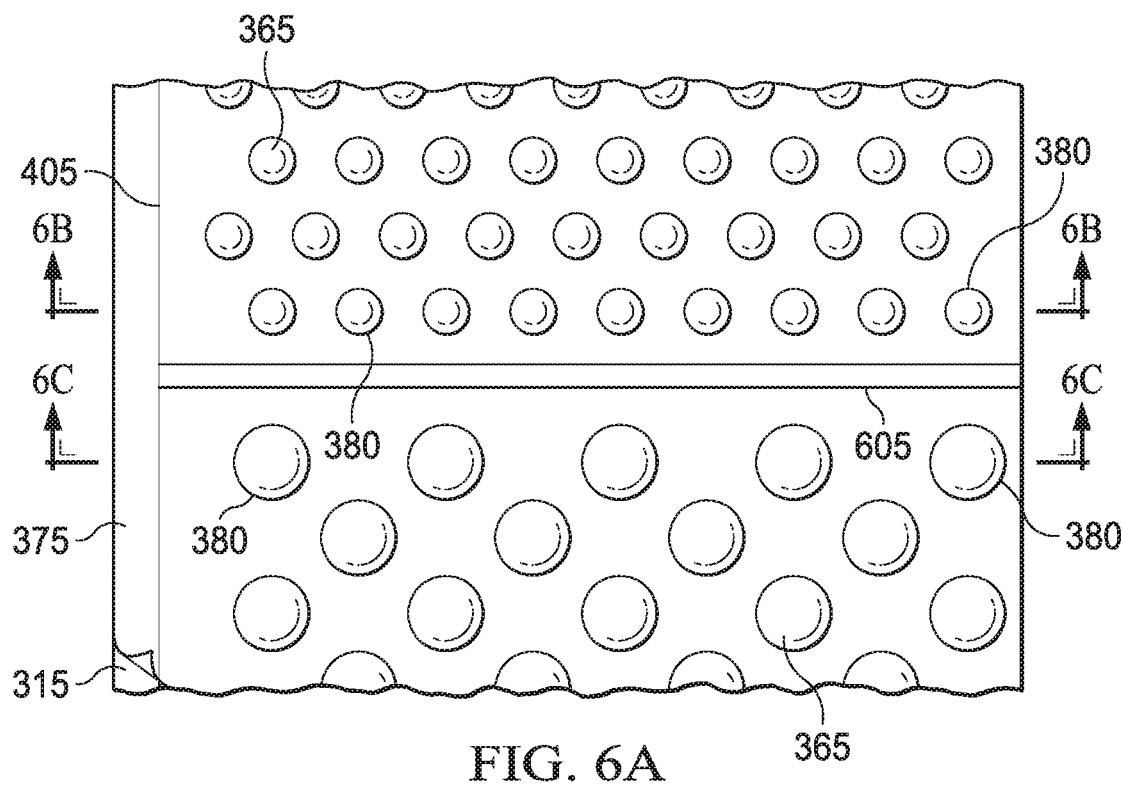
FIGS. 6A, 6B, and 6C illustrate other examples of features that may be associated with some embodiments of a bridge in the therapy system of FIG. 1.
Figure 6B:
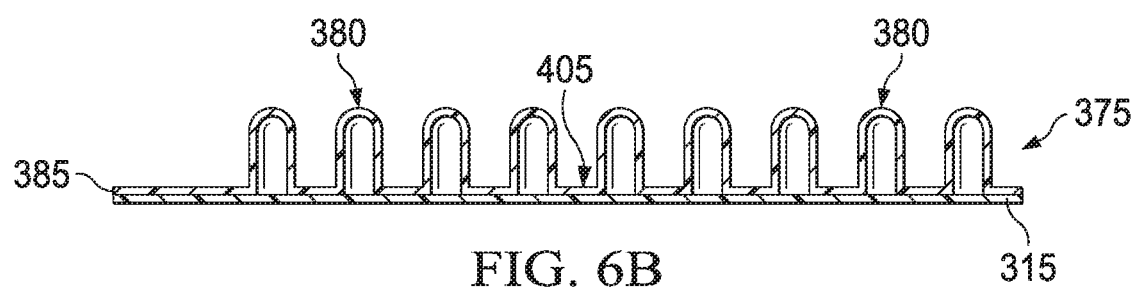
Figure 6C:
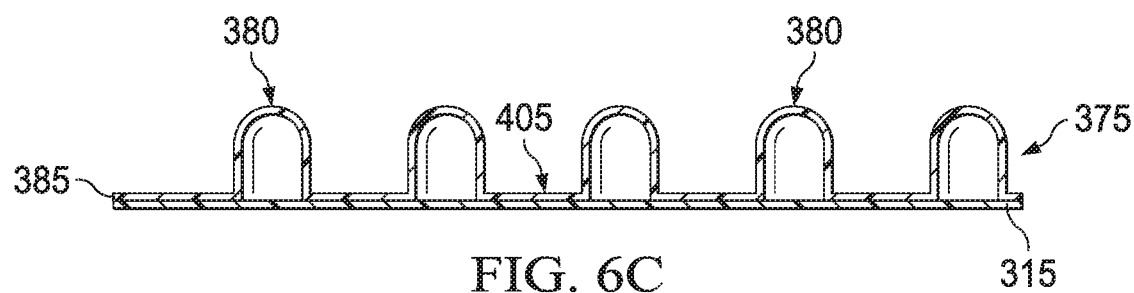

FIGS. 6A, 6B, and 6C illustrate other examples of features that may be associated with some embodiments of the bridge 160. In FIG. 6A, the first layer 315 and the spacer layer 375 define a nested arrangement of the supports 365. The example of FIG. 6A further illustrates that at least some of the supports 365 may additionally or alternatively have different sizes. For example, some of the supports 365 may have a diameter in the range between about 1 mm and about 10 mm, and some of the supports 365 may have a diameter in the range between about 1 mm and about 3 mm. In some embodiments, a wall 605 may be disposed between the some of the supports 365. For example, the wall 605 in the example of FIG. 6A is disposed between the supports 365 having different sizes. The supports 365 having a larger diameter and pitch may increase fluid flow to facilitate the removal of fluids and exudates within the recessed space 360 in some embodiments. In some embodiments, the supports 365 having a smaller diameter and pitch may restrict fluid flow to facilitate pressure sensing within the recessed space 360 while impeding the inflow of fluids and exudates into the first pathway 340. The arrangement and dimensions of the supports 365 may be tailored to manage the delivery of negative pressure to the tissue interface 120 and the measurement of pressure within the recessed space 360.

Figure 7:
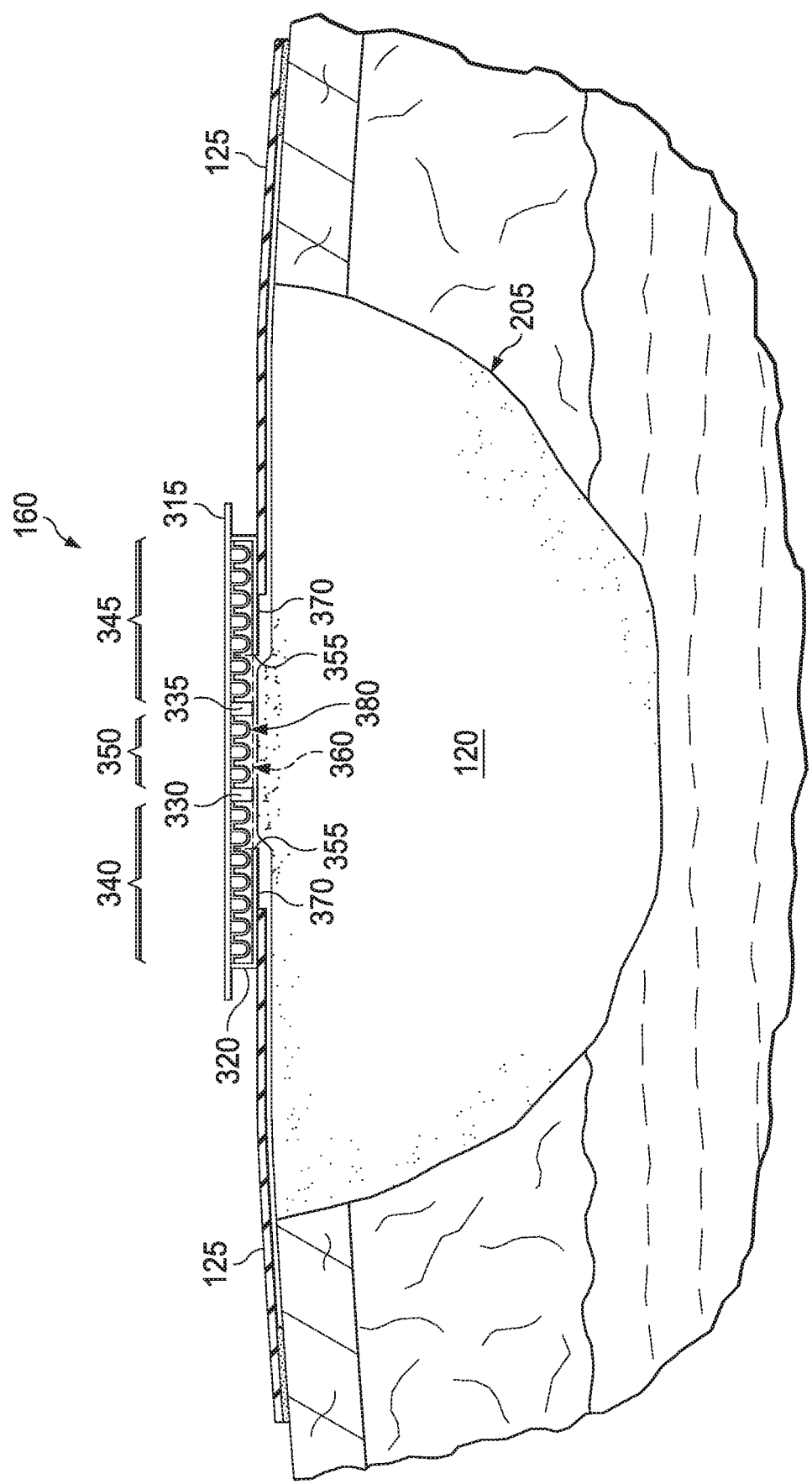
FIG. 7 is a schematic diagram of the bridge of FIG. 3A applied to a tissue site with negative pressure.

FIG. 7 is a schematic diagram of the bridge 160 of FIG. 3A applied to the tissue site 205 with negative pressure. The tissue interface 120 may be in fluid communication with the recessed space 360 through the aperture 355. The affixation surface 370 may be coupled to the cover 125 to seal and fluidly couple the recessed space 360 to the tissue interface 120. In the example of FIG. 7, the first wall 330 and the second wall 335 partially define the first pathway 340, the second pathway 345, and the third pathway 350 between the first layer 315 and the second layer 320.

Within the recessed space 360, the standoffs 380 can extend from the first layer 315 toward the tissue interface 120 and may be adapted to come in direct contact with the tissue interface 120 if negative pressure is applied to the bridge 160. Negative pressure can compress the bridge 160, and the first layer 315 and the second layer 320 can collapse toward each other because of the vacuum created within the standoffs 380. Although the standoffs 380 may change shape or flatten somewhat under negative pressure, the volume of the standoffs 380 remains substantially constant and can maintain fluid flow through the third pathway 350. The standoffs 380 can also provide a cushion to help prevent the sealed spaces of the bridge 160 from collapsing as a result of external forces. The standoffs 380 disposed in the third pathway 350 may be sized and arranged in a pattern that may increase fluid flow of negative pressure being applied to the tissue interface 120 to facilitate the removal of fluids and exudates within the recessed space 360. The standoffs 380 disposed in the first pathway 340 and the second pathway 345 may be sized and arranged in a pattern to facilitate pressure sensing within the recessed space 360 while impeding the inflow of fluids and exudates into the first pathway 340 and the second pathway 345 to reduce blockage conditions.

The standoffs 380 may have a variety of shapes, and may be sized and arranged in different patterns within the sealed space to enhance the delivery of negative pressure to the tissue interface 120 for a specific type of tissue site while optimizing pressure sensing and measurement of the negative pressure within the recessed space 360.

Figure 8:
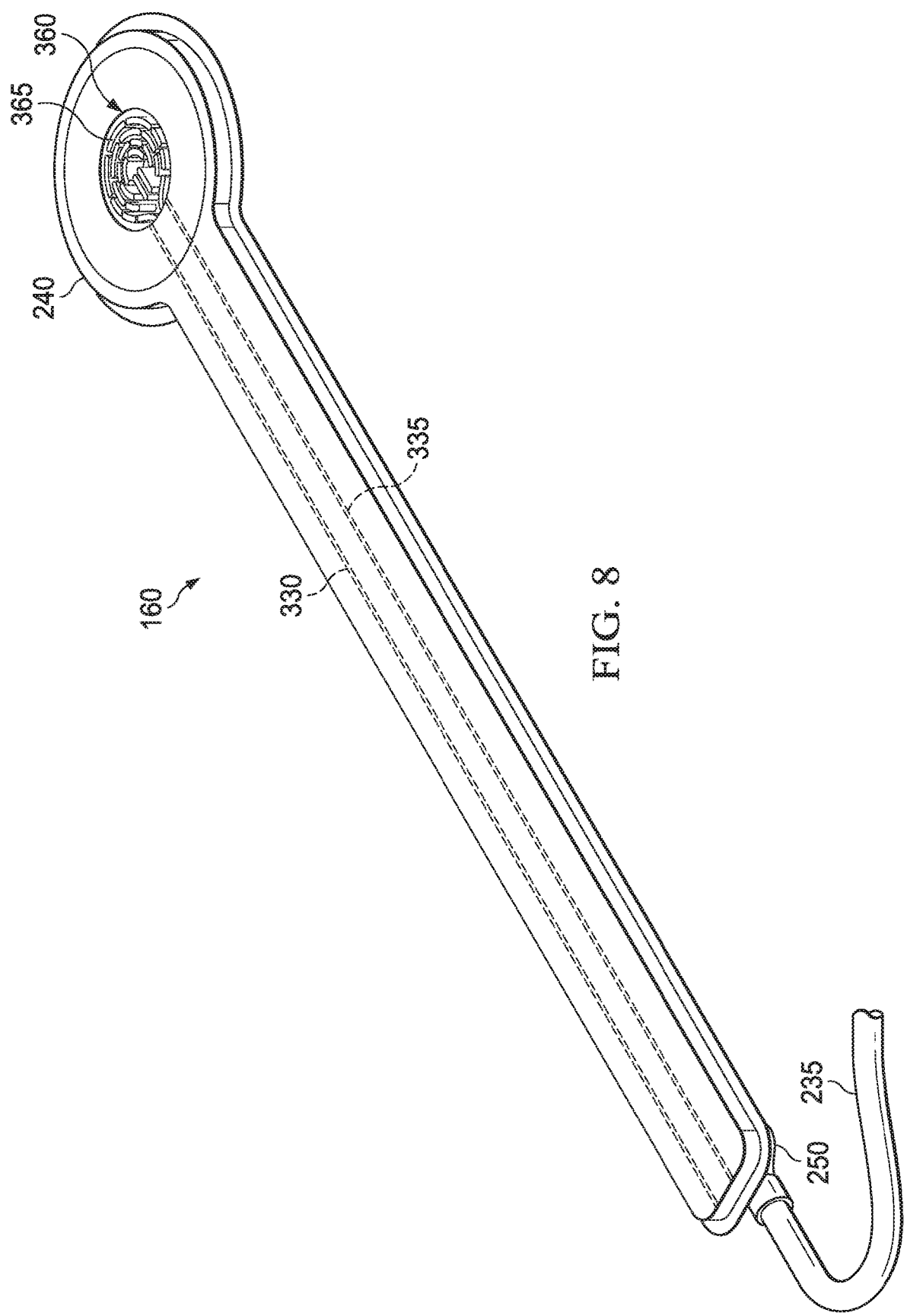
FIG. 8 is a perspective bottom view of another example of a bridge that may be associated with some embodiments of the therapy system of FIG. 1.

FIG. 8 is a perspective bottom view of another example of the bridge 160 having a low-profile structure that may be associated with some embodiments of the therapy system 100. As illustrated in the example of FIG. 8, the first wall 330 and the second wall 335 may extend lengthwise through the bridge 160 between the recessed space 360 and the adapter 250.

Figure 9A:
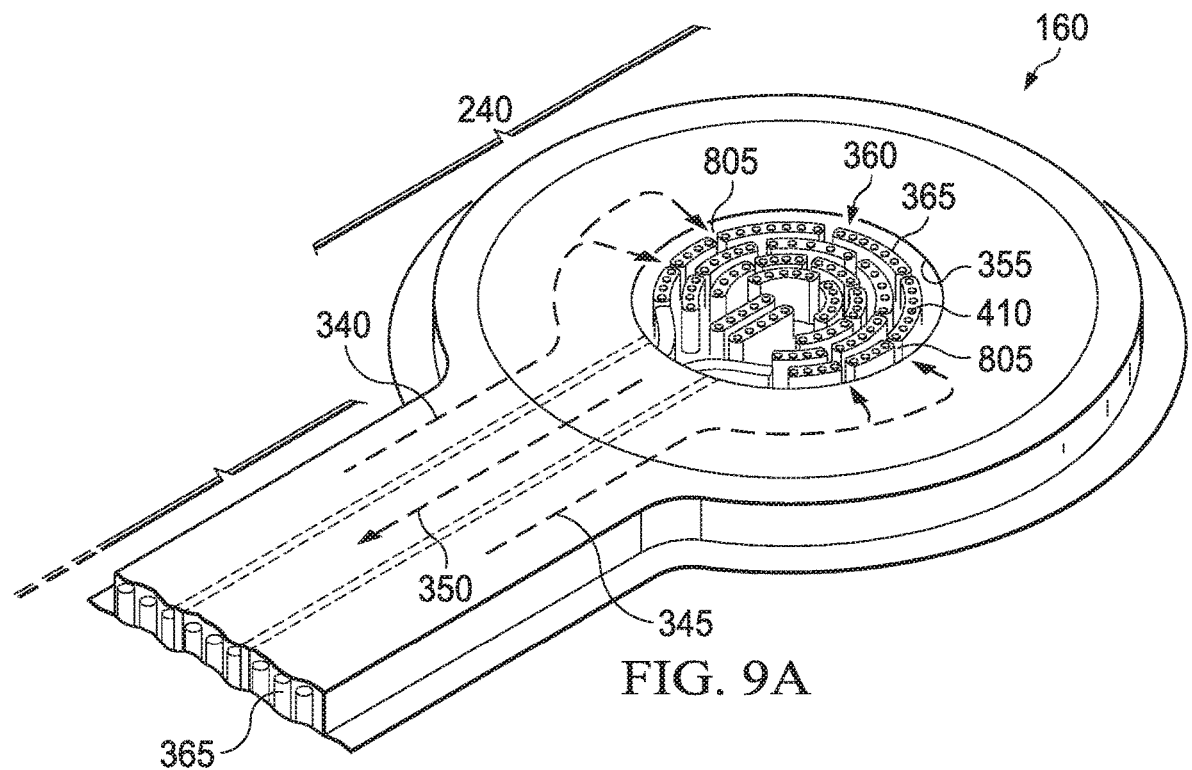
FIG. 9A and FIG. 9B are segmented perspective views of the bridge of FIG. 8.
Figure 9B:
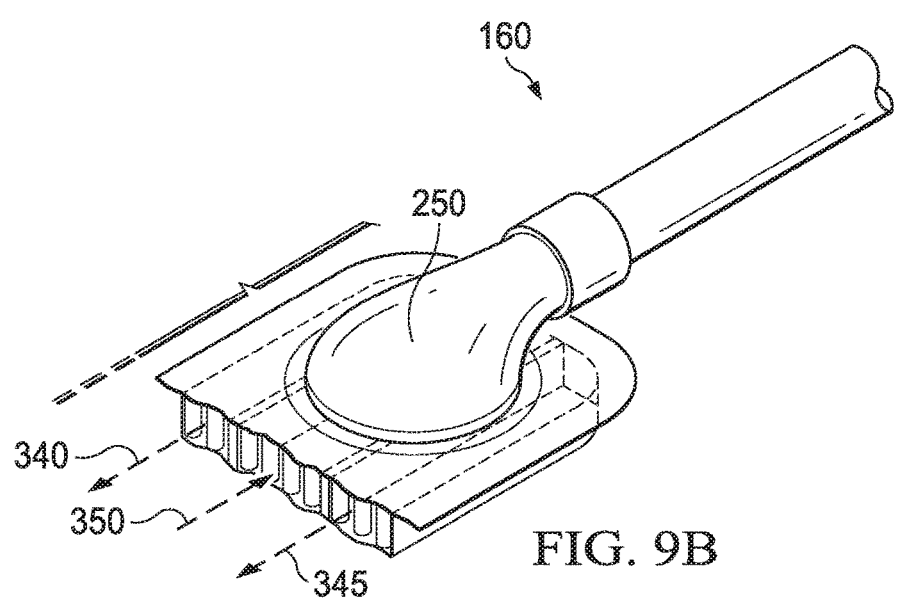

FIG. 9A and FIG. 9B are segmented perspective views of the bridge 160 of FIG. 8, illustrating additional details that may be associated with some examples. FIG. 9A is a bottom perspective view of an example of the applicator 240, illustrating a configuration having a circular profile. FIG. 9B is a top perspective view of an example of the adapter 250, which may have an elbow connector of semi-rigid material in some embodiments.

The aperture 355 of FIG. 9A is generally circular and opens to the recessed space 360. The supports 365 of FIG. 9A may have a generally elongated and arcuate profile and may be arranged in a generally concentric pattern within the recessed space 360. Some embodiments of the supports 365 may also comprise surface features, such as the nodes 410. The supports 365 disposed in the center of the recessed space 360 may be more aligned with the third pathway 350 to increase fluid flow of negative pressure being applied to the tissue interface 120 and facilitate the removal of fluids and exudates within the recessed space 360. In some embodiments, some of the supports 365 may be disposed around the aperture 355 to form a semicircular path opposite the third pathway 350, including spaces 805 between the supports 365. The semicircular alignment of the supports 365 may be positioned within the recessed space 360 to minimize contact with the flow of fluids passing through from the tissue interface 120 to the third pathway 350 if negative pressure is applied. Additionally, the spaces 805 may be sufficiently small for further restricting fluid flow into the first pathway 340 and the second pathway 345, as indicated by the dashed arrows. The spaces 805 can facilitate pressure sensing within the recessed space 360 while impeding the inflow of fluids and exudates into the first pathway 340 and the second pathway 345 to reduce the possibility of blockage. In some embodiments, a portion of the perimeter of the aperture 355 may be welded to an outer ring of the supports 365 to further restrict fluid flow to the first pathway 340 and the second pathway 345 and further impede the inflow of fluids and exudates without inhibiting pressure sensing within the recessed space 360.

Figure 10:
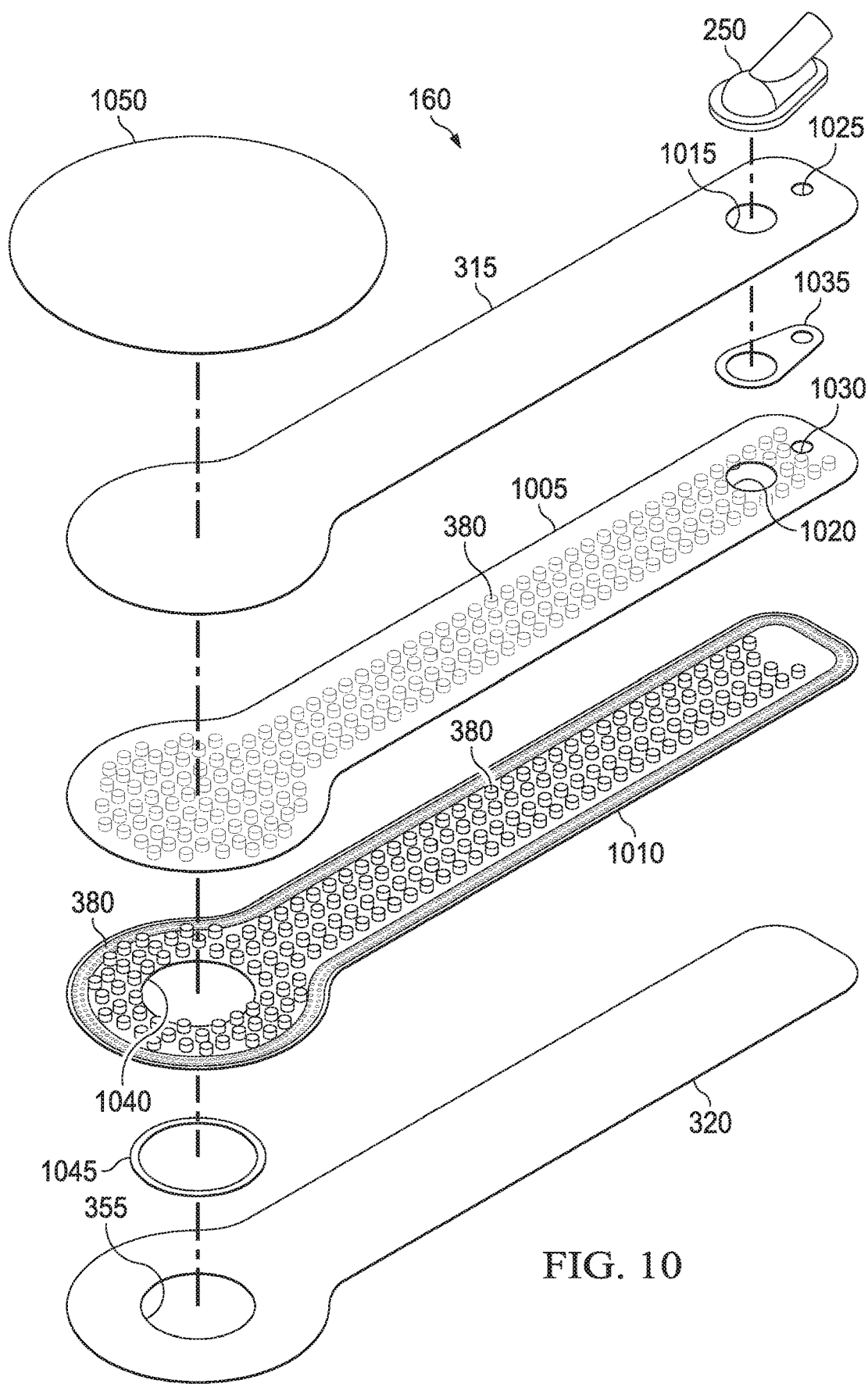
FIG. 10 is an assembly view of another example of a bridge that may be associated with some example embodiments of the therapy system of FIG. 1.

FIG. 10 is an assembly view of another example of the bridge 160 having a low-profile structure that may be associated with some example embodiments of the therapy system 100. In the example of FIG. 10, the bridge 160 comprises two spacer layers—a first spacer layer 1005 and a second spacer layer 1010—disposed between the first layer 315 and the second layer 320. In some embodiments, the first spacer layer 1005 and the second spacer layer 1010 may each be similar to spacer layer(s) 375. For example, standoffs 380 may be formed in each of the first spacer layer 1005 and the second spacer layer 1010. In the example of FIG. 10, the standoffs 380 in the first spacer layer 1005 are configured to extend toward the second spacer layer 1010, and the standoffs 380 in the second spacer layer 1010 are configured to extend toward the first spacer layer 1005. The first layer 315 may have a passage 1015, and the first spacer layer 1005 may have a passage 1020, through which fluids may flow to the adapter 250. The first layer 315 and the first spacer layer 1005 may additionally have a passage 1025 and a passage 1030, respectively, which may also be fluidly coupled to the adapter 250. The bridge 160 may further comprise a fluid exit bond 1035 to prevent leakage of fluids flowing through the passage 1015 and the passage 1020. The second spacer layer 1010 may have an aperture 1040 concentric with the aperture 355 of the second layer 320. The bridge 160 may further comprise a fluid exit bond 1045, which can prevent leakage of fluids flowing through the aperture 355 and the aperture 1040.

In some embodiments, a bridge cover 1050 may provide additional protection and support over the applicator 240 if the bridge 160 is applied to a tissue site. In some embodiments, the bridge cover 1050 may also cover any adhesive that might be exposed from applying the bridge 160 to a tissue site. In some embodiments, the bridge cover 1050 may be similar or analogous to the cover 125. For example, the bridge cover 1050 may be a polymer, such as a polyurethane film.

Figure 11A:
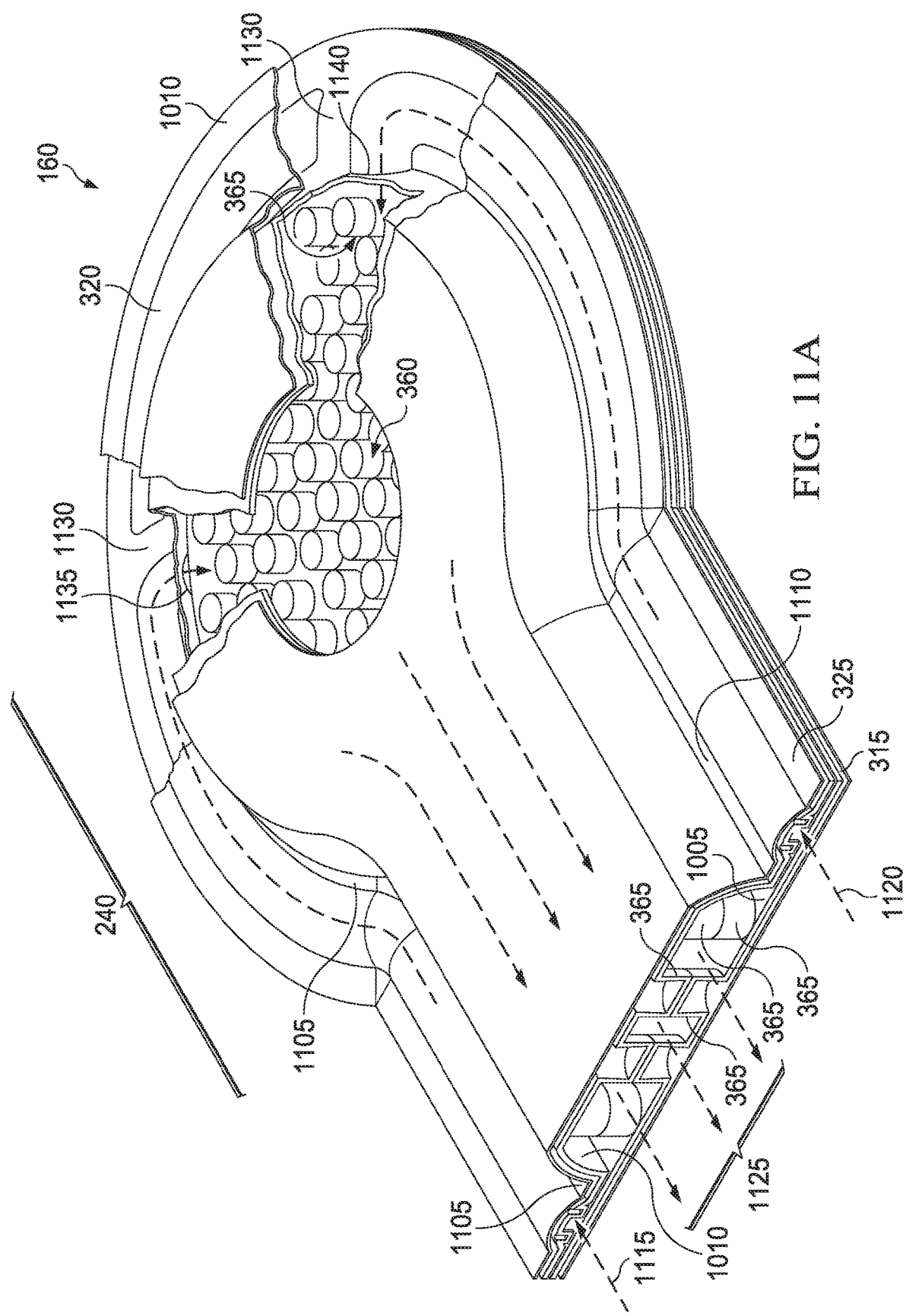
FIG. 11A is a segmented view of an assembled portion of the bridge in the example of FIG. 10, illustrating additional details that may be associated with some embodiments.

FIG. 11A is a segmented view of an assembled portion of the bridge 160 in the example of FIG. 10, illustrating additional details that may be associated with some embodiments. As illustrated in the example of FIG. 11A, the first layer 315, second layer 320, the first spacer layer 1005, and the second spacer layer 1010 may be assembled in a stacked relationship. For example, the first layer 315 may be coupled to the first spacer layer 1005, the second layer 320 may be coupled to the second spacer layer 1010, and a periphery of the first spacer layer 1005 may be coupled to a periphery of the second spacer layer 1010 to form the flange 325. The first spacer layer 1005 and the second spacer layer 1010 can be coupled to form a liquid barrier defining a fluid path along a longitudinal axis of the bridge 160.

Some embodiments of the bridge 160 may additionally comprise at least one barrier or wall, such as a first barrier 1105, interior to the flange 325. The first barrier 1105 may be formed by coupling the first spacer layer 1005 and the second spacer layer 1010. For example, the first spacer layer 1005 may be welded to the second spacer layer 1010 to form the first barrier 1105. In some embodiments, the first barrier 1105 may extend lengthwise through the bridge 160 into the applicator 240 to form at least two fluid paths between the first spacer layer 1005 and the second spacer layer 1010 within the bridge 160. In some examples, the bridge 160 may further comprise a second barrier, such as a second barrier 1110. The second barrier 1110 may be formed by coupling the first spacer layer 1005 and the second spacer layer 1010. In some embodiments, the second barrier 1110 also may extend lengthwise through the bridge 160 into the applicator 240. In some example embodiments, the first barrier 1105 and the second barrier 1110 may comprise a polymeric film coupled between the first layer 315 and the second layer 320. In some other example embodiments, the first barrier 1105 and the second barrier 1110 may comprise a weld (RF or ultrasonic), a heat seal, an adhesive bond, or a combination of any of the foregoing. The first barrier 1105 and the second barrier 1110 may be similar to the first wall 330 and the second wall 335 in some embodiments.

In some embodiments, barriers or walls interior to the flange 325 may form fluid pathways between the first spacer layer 1005 and the second spacer layer 1010. For example, in FIG. 11A, the first barrier 1105 and the second barrier 1110 cooperate with the flange 325 to form a first fluid conductor 1115, a second fluid conductor 1120, and a third fluid conductor 1125. In some applications, the first fluid conductor 1115 and the second fluid conductor 1120 may be coupled to a sensor to measure pressure, and the third fluid conductor 1125 may be coupled to a negative-pressure source. In some example embodiments, the first fluid conductor 1115 and the second fluid conductor 1120 may have a height having a value in a range between about 0.25 mm and about 3 mm. In some example embodiments, the first fluid conductor 1115 and the second fluid conductor 1120 may have a width having a value in a range between about 1 mm and about 7.5 mm. Thus, the first fluid conductor 1115 and the second fluid conductor 1120 may have a cross-sectional area having a value in a range between about 0.17 mm$^2$ and 16.77 mm$^2$. In some embodiments, the first fluid conductor 1115 and the second fluid conductor 1120 may have a cross-sectional area having a value in a range between about 0.1 mm$^2$ and 18 mm$^2$.

In some examples, each of the first barrier 1105 and the second barrier 1110 may extend an angular distance around the proximal end of the applicator 240 and cooperate with blocking walls of the flange 325, such as blocking walls 1130, to form extensions of the first fluid conductor 1115 and the second fluid conductor 1120. The extensions may be fluidly coupled to the recessed space 360. In the example of FIG. 11A, the first fluid conductor 1115 and the second fluid conductor 1120 are fluidly coupled to the recessed space 360 through passages, such as a through-hole 1135 and a through-hole 1140, respectively. In some examples, at least some of the supports may be disposed in one or both of the first fluid conductor 1115 and the second fluid conductor 1120. For example, some of the supports may be formed by the standoffs 380 disposed between the flange 325 and the first barrier 1105, and between the flange 325 and the second barrier 1110. Additionally or alternatively, the thickness of the spacer layer 1010 may be increased to provide additional structural support to the first fluid conductor 1115 and the second fluid conductor 1120. In some examples, the first fluid conductor 1115 and the second fluid conductor 1120 may comprise or be formed by tubes through or along the bridge 160. Some configurations may not have the first fluid conductor 1115 or the second fluid conductor 1120, or may have only one of the first fluid conductor 1115 and the second fluid conductor 1120.

Each of the first barrier 1105 and the second barrier 1110 can extend at least partially around the proximal end of the applicator 240 that form the first fluid conductor 1115 and the second fluid conductor 1120. For example, in some embodiments each of the first barrier 1105 and the second barrier 1110 can extend from about 45° to about 315° from the center of the third fluid conductor 1125 where the third fluid conductor 1125 is in fluid communication with the recessed space 360. In some embodiments, the angular distance may be different for each of the first fluid conductor 1115 and the second fluid conductor 1120. For example, the angular distance for each of the first fluid conductor 1115 and the second fluid conductor 1120 may be about 60° and 210°, respectively, from the third fluid conductor 1125.

In some example embodiments, the through-hole 1135 and the through-hole 1140 may be separated from each other by an angular distance of at least 90°, extending around the applicator 240 in a direction away from the third fluid conductor 1125. The spacing and disposition of the through-hole 1135 and the through-hole 1140 from each other, and from the third fluid conductor 1125, can allow the first fluid conductor 1115 and the second fluid conductor 1120 to better avoid the flow of fluids passing through from the tissue interface 120 to the third fluid conductor 1125 when negative pressure is applied. Additionally, the through-hole 1135 and the through-hole 1140 may be sufficiently small for further restricting fluid flow into the first fluid conductor 1115 and the second fluid conductor 1120. In some embodiments, the through-hole 1135 and the through-hole 1140 may have a cross-sectional area having a value in a range between about 0.17 mm$^2$ and 16.77 mm$^2$. In some embodiments, the through-hole 1135 and the through-hole 1140 may have a cross-sectional area having a value in a range between about 0.1 mm$^2$ and 18 mm$^2$ to further restrict fluid flow to the first fluid conductor 1115 and the second fluid conductor 1120 and impede the inflow of fluids and exudates without inhibiting pressure sensing within the recessed space 360.

Figure 11B:
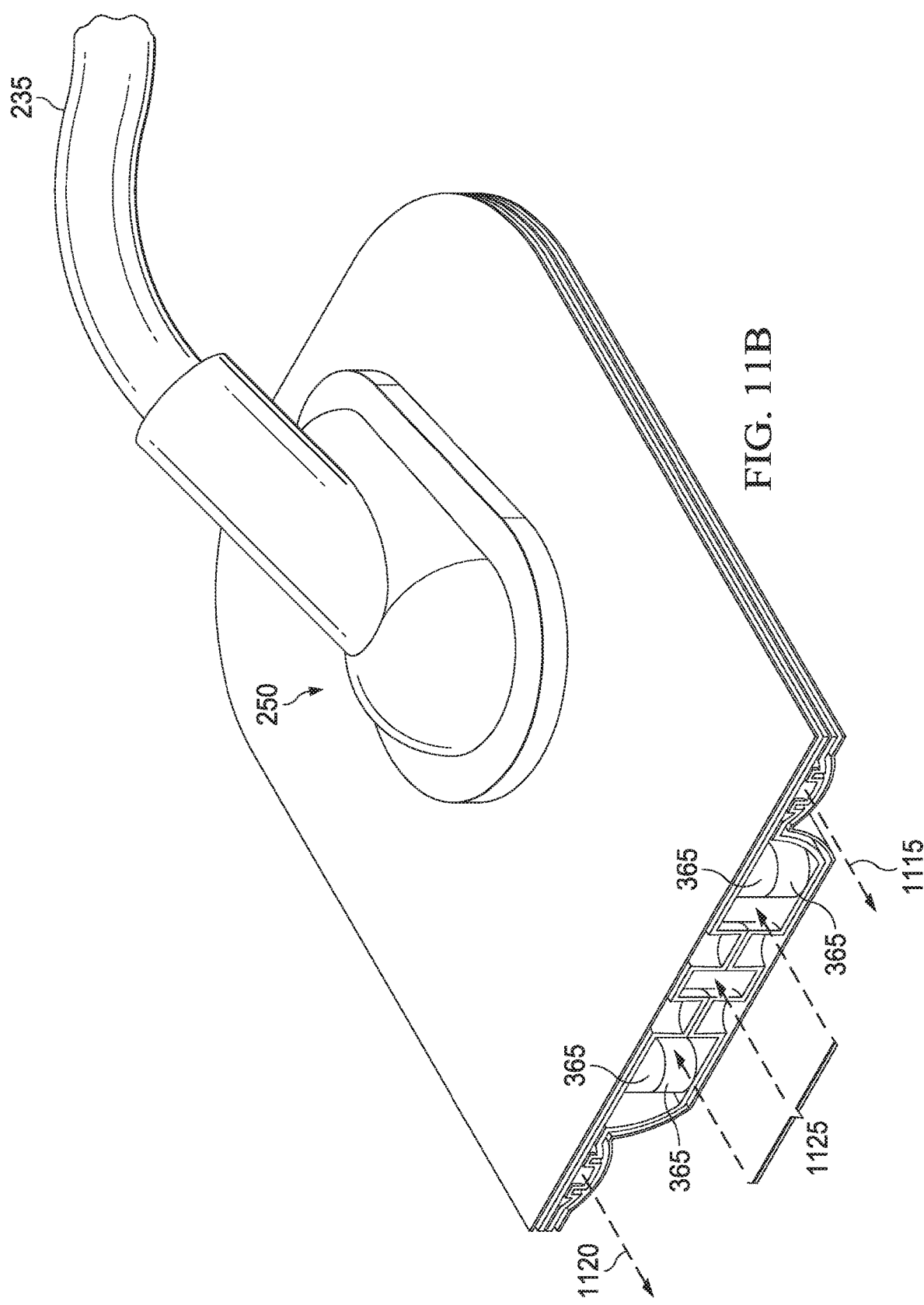
FIG. 11B is a segmented perspective view of portion of the bridge in the example of FIG. 10, illustrating additional details that may be associated with some embodiments.

FIG. 11B is a segmented perspective view of portion of the bridge 160 in the example of FIG. 10, illustrating additional details that may be associated with some embodiments. FIG. 11B further illustrates an example of the adapter 250 and the conduit 235 coupled to the bridge 160. Each of the first fluid conductor 1115 and the second fluid conductor 1120 may be fluidly coupled directly to the conduit 235 in some examples. In other examples, both of the first fluid conductor 1115 and the second fluid conductor 1120 may be fluidly coupled to a single space (not shown) within the adapter 250, which can be fluidly coupled to the conduit 235.

In the example of FIG. 11A and FIG. 11B, both the first fluid conductor 1115 and the second fluid conductor 1120 are fluidly separate from and parallel to the third fluid conductor 1125. The parallel orientation can minimize the vertical profile of the bridge 160, while still being resistant to collapsing under pressure that could block fluid flow through the fluid pathways.

Figure 12A:
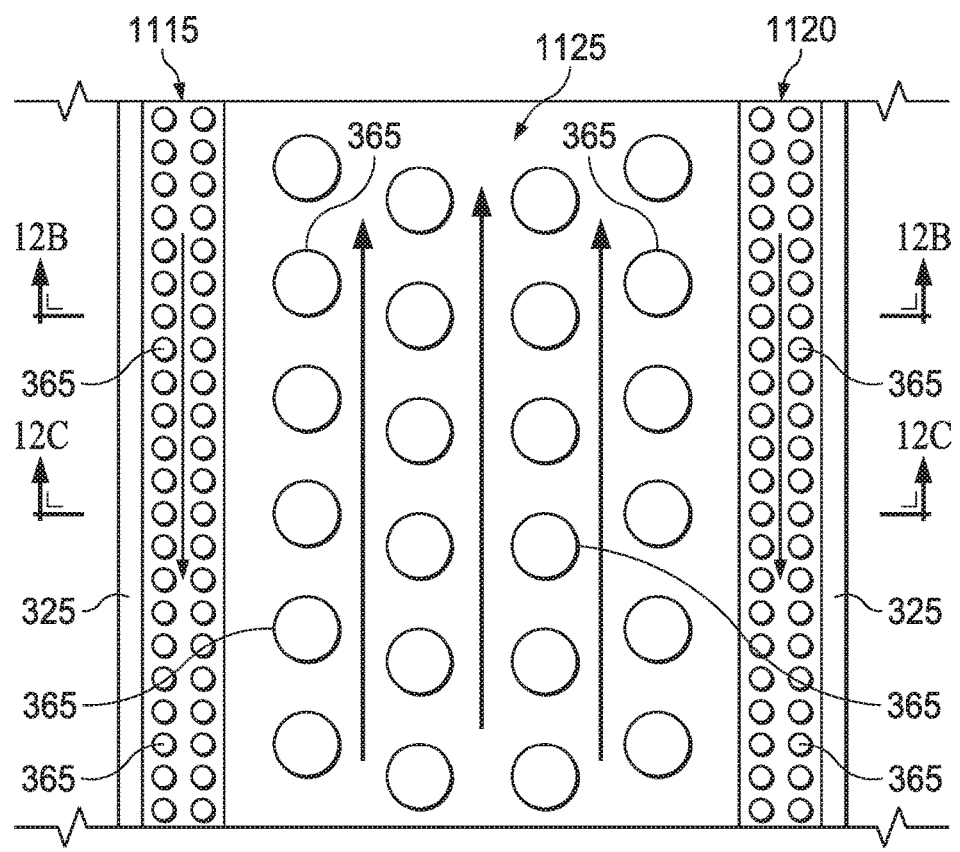
FIG. 12A is a schematic view of an example configuration of fluid pathways in the bridge of FIG. 10 as assembled, illustrating additional details that may be associated with some embodiments.
Figure 12B:
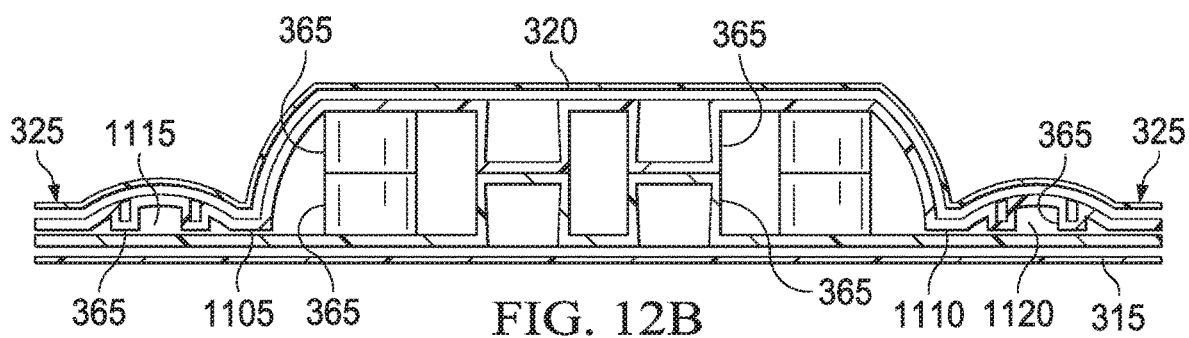
FIG. 12B is a schematic view taken along line 12B-12B of FIG. 12A.
Figure 12C:
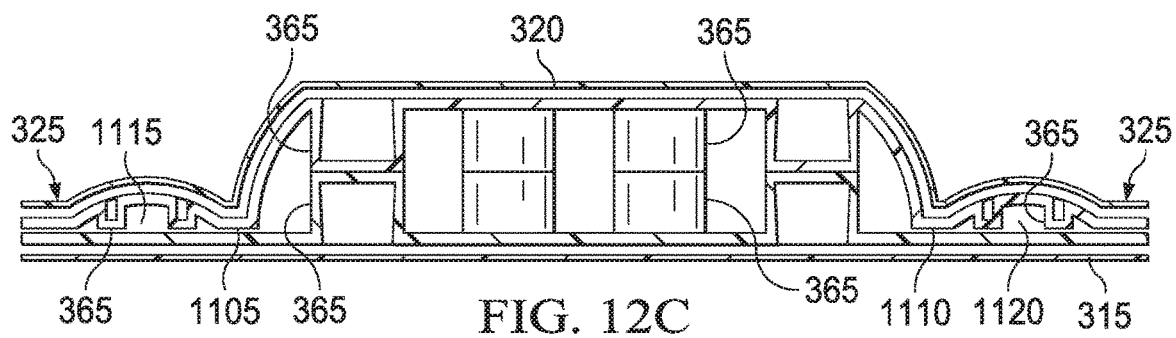
FIG. 12C is a schematic view taken along line 12C-12C of FIG. 12A.

FIG. 12A is a schematic view of an example configuration of fluid pathways in the bridge 160 of FIG. 10 as assembled, illustrating additional details that may be associated with some embodiments. FIG. 12B is a schematic view taken along line 12B-12B, and FIG. 12C is a schematic view taken along line 12C-12C. The supports 365 may have a variety of shapes, and may be sized and arranged in different patterns within the third fluid conductor 1125. For example, as illustrated in the examples of FIG. 12B and FIG. 12C, some of the supports 365 may extend from the first layer 315 and some of the supports 365 may extend from the second layer 320. In some embodiments, some of the supports 365 may be opposingly aligned. For example, at least some of the supports 365 can extend from the first layer 315 towards some of the supports 365 extending from the second layer 320, and some of the supports 365 in opposition may contact each other. In some embodiments, the bridge 160 may include more than one row of the supports 365. In the example of FIG. 12A, the bridge 160 has four rows of the supports 365, and the supports 365 forming outside rows are offset or staggered from the supports 365 forming the two inside rows. Each of the first barrier 1105 and the second barrier 1110 cooperate with the flange 325 to form the first fluid conductor 1115 and the second fluid conductor 1120. In some embodiments, some of the supports 365 may be disposed within one or both of the first fluid conductor 1115 and the second fluid conductor 1120.

The supports 365 disposed in the third fluid conductor 1125 may have a larger diameter and pitch than the supports 365 in the first fluid conductor 1115 and the second fluid conductor 1120, and may increase fluid flow to facilitate the removal of fluids and exudates within the recessed space 360. The supports 365 in the first fluid conductor 1115 and the second fluid conductor 1120 may have a noticeably smaller diameter and pitch than the supports 365 in the third fluid conductor 1125, and may restrict fluid flow to facilitate pressure sensing within the recessed space 360 while impeding the inflow of fluids and exudates into the first fluid conductor 1115 and the second fluid conductor 1120. The arrangement and dimensions of the supports 365 may be tailored to manage the delivery of negative pressure to the tissue interface 120 and the measurement of pressure within the recessed space 360.

Figure 13A:
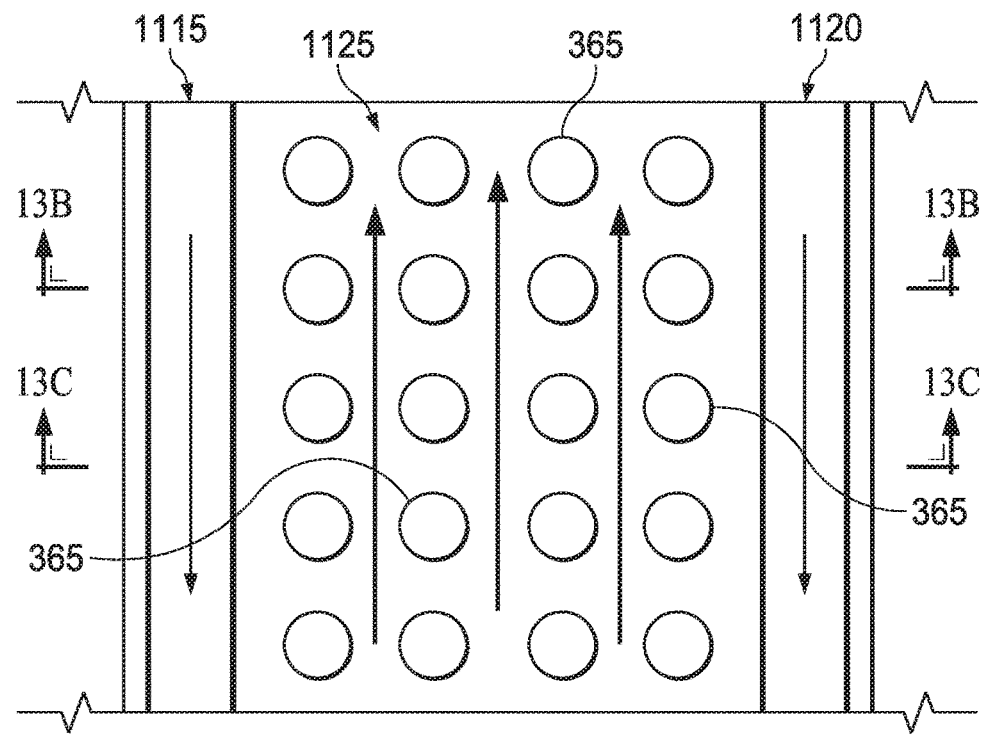
FIG. 13A is a schematic view of another example configuration of fluid pathways in the bridge of FIG. 10 as assembled, illustrating additional details that may be associated with some embodiments.
Figure 13B:
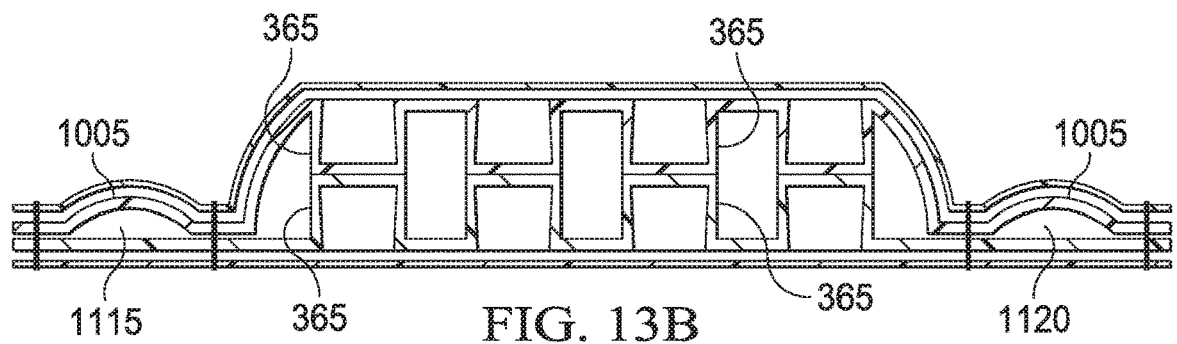
FIG. 13B is a schematic view taken along line 13B-13B of FIG. 13A.
Figure 13C:
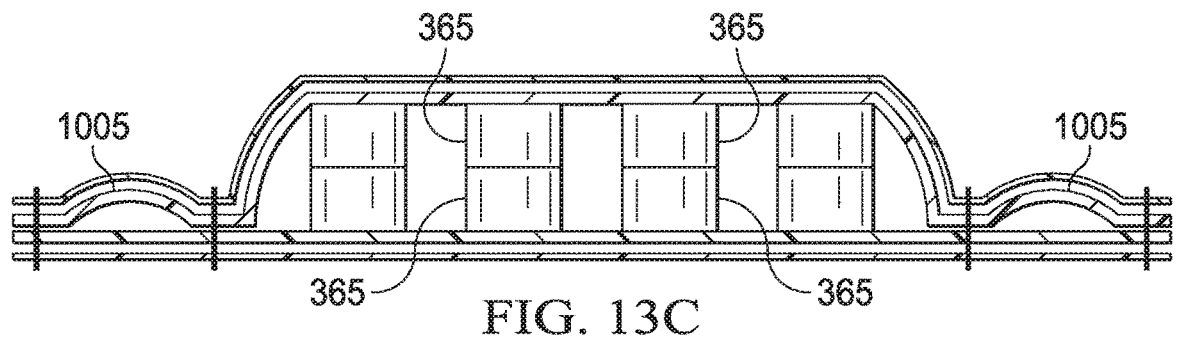
FIG. 13C is a schematic view taken along line 13C-13C of FIG. 13A.

FIG. 13A is a schematic view of another example configuration of fluid pathways in the bridge 160 of FIG. 10 as assembled, illustrating additional details that may be associated with some embodiments. FIG. 13B is a schematic view taken along line 13B-13B, and FIG. 13C is a schematic view taken along line 13C-13C. The example of FIG. 13A includes four rows of the supports 365, which are aligned both horizontally and vertically rather than being offset or staggered with each other. In some embodiments, the first fluid conductor 1115 and the second fluid conductor 1120 may be opened and supported by increasing the thickness of the first spacer layer 1005.

Figure 14:
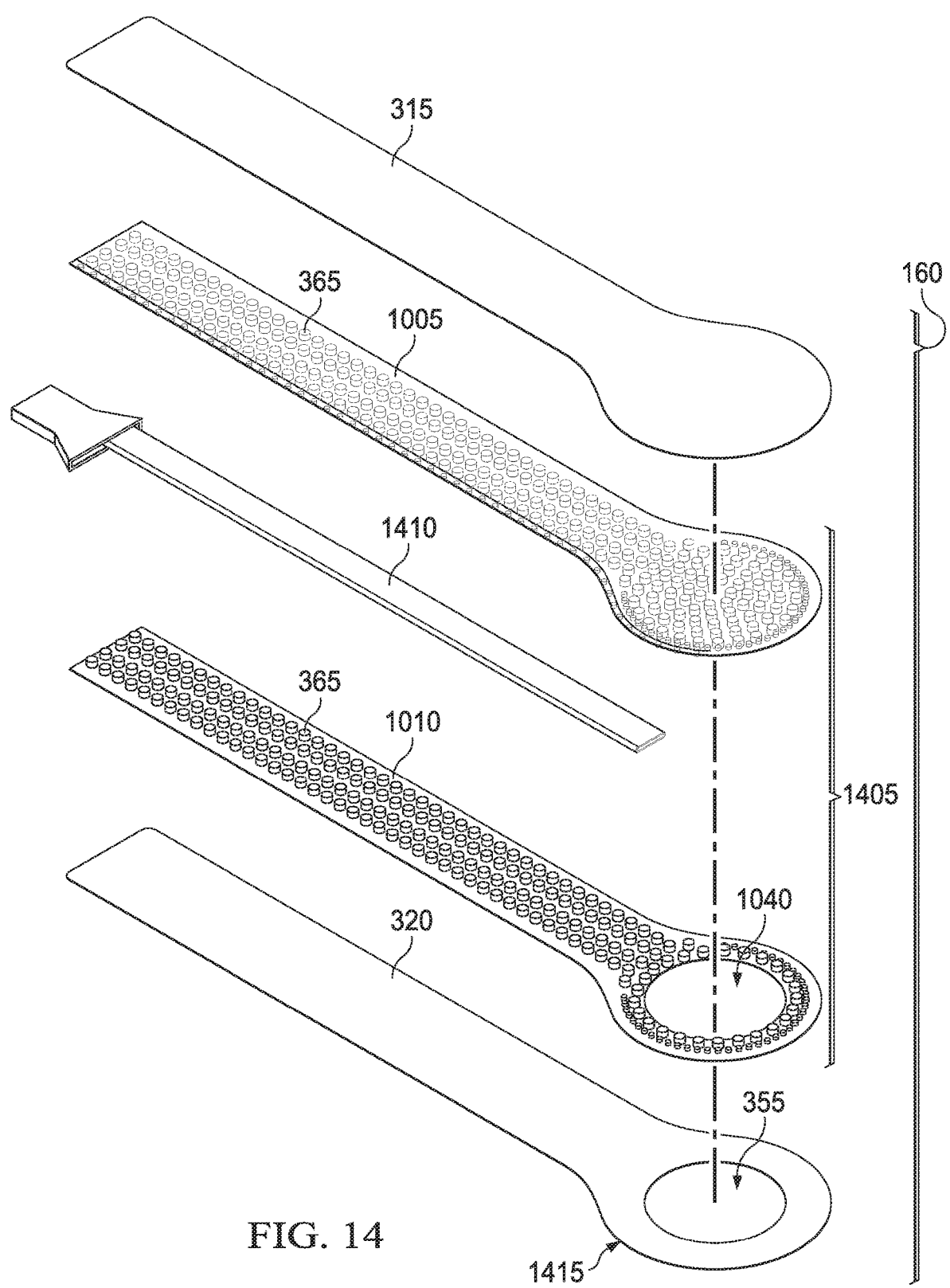
FIG. 14 is an assembly view of another example of a bridge for negative pressure therapy, which has integrated instillation, illustrating additional details that may be associated with some embodiments.

FIG. 14 is an assembly view of another example of the bridge 160 having a low-profile structure that may be associated with some example embodiments of the therapy system 100. The bridge 160 in FIG. 14 may be configured to provide installation and negative-pressure therapy. For example, a negative-pressure pathway 1405 may be formed in the bridge 160, and an installation pathway may be located within the negative-pressure pathway 1405. In the embodiment shown in FIG. 14, the bridge 160 may be similar to that shown in FIG. 10, but may further comprise an installation pathway within an installation conduit 1410 located within the negative-pressure pathway 1405.

For example, the bridge 180 in FIG. 14 may comprise the first layer 315, the first spacer layer 1005, the installation conduit 1410 forming the installation pathway, the second spacer layer 1010, and the second layer 320. In FIG. 14, the installation conduit 1410 may be stacked between the first spacer layer 1005 and the second spacer layer 1010, with the supports 365 of the first spacer layer 1005 and the supports 365 of the second spacer layer 1010 extending inward towards the installation conduit 1410. The first layer 315 may be adjacent to and in stacked relationship with the first spacer layer 1005, opposite the installation conduit 1410. The second layer 320 may be adjacent to and in stacked relationship with the second spacer layer 1010, opposite the installation conduit 1410. The first layer 315 and the second layer 320 may be sealed together about the perimeter, forming the enclosed negative-pressure pathway 1405 supported by the first spacer layer 1005 and the second spacer layer 1010, with the installation conduit 1410 located within the negative-pressure pathway 1405 and between the supports 365 of the first spacer layer 1005 and the second spacer layer 1010.

In FIG. 14, the second layer 320 may comprise an aperture 355 configured to allow fluid communication between the negative-pressure pathway 1405 and the ambient environment. The aperture 355 in FIG. 14 may be located in a distal end 1415 of the bridge 160. Some embodiments may also comprise a second aperture 1040 located in the second spacer layer 1010 which may be concentric with the aperture 355 of the second layer 320. In some embodiments, the first layer 315 and the second layer 320 may be coupled to form the enclosed space of the negative-pressure pathway 1405 between the first layer 315 and the second layer 320. In some embodiments, the first layer 315 and the second layer 320 may each be formed of a film. Other embodiments may form the negative-pressure pathway 1405 as an open pathway using only a single spacer layer. Other embodiments may form the negative-pressure pathway 1405 by sealing the first spacer layer 1005 to the second spacer layer 1010 about the perimeter, for example without the need for any exterior film layers. Other embodiments may form the negative-pressure pathway 1405 between the first layer 315 and the second layer 320, while having the plurality of supports located therebetween without any spacer layer. For example, longitudinal tubular supports might be located between the first layer 315 and the second layer 320 in some alternate embodiments, along with the installation conduit 1410.

In some embodiments, the installation pathway and the negative pressure pathway may be located within a single bridge 160, as shown in FIG. 14. In some embodiments, the bridge 160 may be configured with a low profile. For example, the bridge 160 may have a height of approximately 5 millimeters. Some embodiments may have a height of less than approximately 5 millimeters. Some embodiments of the bridge 160 may have a length from approximately 200 millimeters to 500 millimeters.

FIG. 15A is a plan view of the bridge 160 of FIG. 14, illustrating additional details that may be associated with some embodiments. As shown in FIG. 15A, the negative-pressure pathway 1405 is supported as an open pathway by the plurality of supports 365. In some embodiments, the plurality of supports 365 may be configured to support the negative-pressure pathway 1405 substantially along its entire length and/or width. For example, the supports 365 may be co-extensive with the negative-pressure pathway 1405. In some embodiments, the plurality of supports 365 may be arranged in rows, and the rows may be aligned and may extend longitudinally. For example, the rows may extend the length of the bridge 160, with longitudinally extending spaces of the negative-pressure pathway 1405 separating the rows. The row configuration of supports 365 may allow fluid flow longitudinally from one end of the negative-pressure pathway 1405 to the other, for example when the bridge 160 is under compression. For example, in the row configuration of supports 365, the longitudinally extending spaces may provide unobstructed flow channels of the negative-pressure pathway 1405 between the rows of supports 365.

In some embodiments, the bridge 160 may comprise a port 1505 configured to fluidly couple the negative-pressure pathway 1405 to a negative pressure source and fluidly couple the installation conduit 1410 to an installation source. For example, the port 1505 may be located in a proximal end 1510 of the bridge 160, and the negative-pressure pathway 1405 and the installation conduit 1410 comprising the installation pathway may each extend from the port 1505 to approximately the aperture in the distal end 1415. Some embodiments of the port 1505 may be similar to the adapter 250.

Some embodiments of the bridge 160 may comprise a pressure-sensing pathway 1515 that extends parallel to the negative-pressure pathway 1405. In some embodiments, the pressure-sensing pathway 1515 may be similar to the first pathway 340 or the second pathway 345 in FIG. 3A or the first fluid conductor 1115 or second fluid conductor 1120 in FIG. 11A. The pressure-sensing pathway 1515 may be pneumatically isolated from the negative-pressure pathway 1405 and the installation pathway 1410 except through the aperture in the distal end 1415 of the bridge 160. For example, the port 1505 may further be configured to fluidly couple the pressure-sensing pathway 1515 to a pressure sensor, and the pressure-sensing pathway 1515 may extend from the port 1505 to approximately the aperture. In some embodiments, the pressure-sensing pathway 1515 may be formed by a barrier 1105 between the inner surface of the first layer 315 and the inner surface of the second layer 320 of the negative-pressure pathway 1405, for example forming the pressure-sensing pathway 1515 within the enclosed space of the negative-pressure pathway 1405. In some embodiments, a plurality of pressure-pathway supports 1520 may be located in the pressure sensing pathway. In FIG. 15A, for example, the plurality of pressure-pathway supports 1520 in the pressure-sensing pathway 1515 may be smaller than the plurality of supports 365 in the negative-pressure pathway 1405, and may be configured to support the pressure-sensing pathway 1515 against collapse.

FIG. 15B is a schematic longitudinal cross-section slice view of the bridge 160 of FIG. 15A, illustrating additional details that may be associated with some embodiments. FIG. 15B illustrates the distal end 1415 of the bridge 160 and shows the installation conduit 1410 located within the negative-pressure pathway 1405 and extending longitudinally in the negative-pressure pathway 1405. For example, the installation conduit 1410 may extend substantially the length of the negative-pressure pathway 1405. The installation conduit 1405 may extend from the port to the recessed space 360 or aperture 355 in some embodiments. The installation conduit 1410 may form an installation pathway 1525, for example with the installation pathway 1525 in FIG. 15B located within the installation conduit 1410. The installation pathway 1525 may be configured to allow flow of installation fluid during the installation process. As shown in FIG. 15B, the plurality of supports 365 of the bridge 160 may comprise a first plurality of supports 1425 and a second plurality of supports 1430. The installation pathway 1525 may be located between the first plurality of supports 1425 and the second plurality of supports 1430. In some embodiments, the first plurality of support 1425 may be opposingly aligned with the second plurality of supports 1430, for example to support the negative-pressure pathway 1405. The installation pathway 1525 may be located between at least a portion of the first plurality of supports 1425 and the second plurality of supports 1430. In some embodiments, the first spacer layer 1005 may comprise the first plurality of supports 1425, and the second spacer layer 1010 may comprise the second plurality of supports 1430. For example, the first plurality of supports 1425 may extend inward from an inner surface of the first spacer layer 1005, and the second plurality of supports 1430 may extend inward from an inner surface of the second spacer layer 1010. The first plurality of supports 1425 and the second plurality of supports 1430 may each be aligned into longitudinally extending rows. For example, the first plurality of supports 1425 may be aligned into rows that match the rows of the second plurality of supports 1430, so that the first plurality of supports 1425 may be opposingly aligned and stacked with the second plurality of supports 1430.

In some embodiments, the installation pathway 1525 may be configured to fluidly communicate with the negative-pressure pathway 1405 through the recessed space 360 in the negative-pressure pathway 1405. In some embodiments, the recessed space 360 may be configured to fluidly communicate with the ambient environment through the aperture 355 in the second layer. For example, the installation pathway 1525 may be configured to interact with the negative-pressure pathway 1405 so that at least a portion of the installation pathway 1525 collapses upon application of negative pressure to the negative-pressure pathway 1405. In some embodiments, the negative-pressure pathway 1405 and the installation pathway 1525 may each comprise enclosed conduits configured for fluid transfer from one end to another end of the bridge 160. For example, the negative-pressure pathway 1405 and the installation pathway 1525 may each comprise a separate enclosed space for fluid flow from the proximal end 1510 to the distal end 1415 of the bridge 160. In some embodiments, the supports 365 may be located within the enclosed space of the negative-pressure pathway 1405.

In some embodiments, the negative-pressure pathway 1405 and the installation pathway 1525 may be pneumatically isolated from each other and/or the ambient environment except through the recessed space 360 and/or the aperture 355 in the distal end 1415 of the bridge 160. For example, the installation pathway 1525 may be pneumatically isolated from the negative-pressure pathway 1405 except through the recessed space 360 in the distal end of the negative-pressure pathway 1405. In some embodiments, the installation pathway 1525 may interact with the negative-pressure pathway 1405 pneumatically through the recessed space 360, thereby providing fluid communication. In the example of FIG. 15B, the distal end of the installation pathway 1525 may be in fluid communication with the negative-pressure pathway 1405 through the recessed space 360, allowing any negative pressure that is applied to the negative-pressure pathway 1405 to also operate on the installation pathway 1525 in a way that may cause at least a portion of the installation pathway 1525 to collapse. For example, the recessed space 360 in the distal end of the negative-pressure pathway 1405 may be in fluid communication with the open distal end of the installation pathway 1525. In some embodiments, the recessed space 360 may comprise the aperture 355. For example, the recessed space 360 in FIG. 15B may comprise the aperture 355 in conjunction with the second aperture 1040. In some embodiments, the aperture 355 may be configured to allow fluid communication between the recessed space 360 and the ambient environment. In some embodiments, the negative-pressure pathway 1405 and/or the installation pathway 1525 may be in fluid communication with the ambient environment through the aperture 355. For example, the negative-pressure pathway 1405 and the installation pathway 1525 may be pneumatically isolated from the ambient environment except through the aperture 355 and/or the second aperture 1040.

In some embodiments, the installation pathway 1525 and the negative-pressure pathway 1405 may interact through contact of the supports 365 of the negative-pressure pathway 1405 with the installation pathway 1525. For example, as negative-pressure is applied to the negative-pressure pathway 1405, the supports 365 may clamp down on the installation pathway 1525, which may collapse at least a portion of the installation pathway 1525. In some embodiments, at least a portion of the installation pathway 1525 may collapse across the width of the installation pathway 1525 upon application of negative pressure, for example due to clamping of supports and/or suction within the installation pathway from negative-pressure.

In some embodiments, collapse of the installation pathway 1525 may be sufficient to close the installation pathway 1525, substantially preventing fluid flow through the installation pathway 1525. For example, collapse of the installation pathway 1525 may operate to prevent siphoning of installation fluid when negative pressure is applied to the negative-pressure pathway 1405. In some embodiments, the installation pathway 1525 may comprise a collapsible conduit, for example configured to interact with the negative-pressure pathway 1405 so that the collapsible installation conduit 1410 collapses along its entire length upon application of negative pressure to the negative-pressure pathway 1405. For example, the installation pathway 1525 in FIG. 15B may comprise no internal support, such that there may be no installation supports within the installation pathway 1525. Instead, the installation pathway 1525 may be configured to collapse, for example when there is no fluid pressure within the installation pathway 1525 and/or when the installation pathway 1525 experiences negative pressure. By way of example, the collapsible installation conduit 1410 may comprise a thin polyurethane film tube, which may have a material thickness of the polyurethane material from approximately 30 to 80 micron.

In some embodiments, each of the supports 365 of the first spacer layer 1005 may comprise a hollow standoff 380, and the first layer 315 may be sealed to the first spacer layer 1005 to maintain internal pressure within the plurality of hollow standoffs 380. In some embodiments, each of the plurality of supports 365 may comprise a standoff 380 and a base, with the standoff having a closed surface extending away from the base. Similarly, each of the second plurality of supports 1430 of the second spacer layer 1010 may comprise a hollow standoff 380, and the second layer 320 may be sealed to the second spacer layer 1010 to maintain internal pressure within the standoffs 380 of the second plurality of supports 1430. In some embodiments, the first layer 315 and/or the second layer 320 may comprise a polyurethane film from approximately 80 to 120 micron in thickness. In some embodiments, the first spacer layer 1005 and/or the second spacer layer 1010 may be thermoformed structures with integral open pathway features, such as supports 365. In some embodiments, the thermoformed structures may comprise thermoplastic polyurethane, for example thermoplastic polyurethane film from approximately 200 to 500 microns in thickness. The supports 365 may comprise a variety of shapes, for example substantially circular, hexagonal, oval, triangular, and/or square. In some embodiments, the standoffs 380 may each comprise a blister, a bubble, or a cell. In some embodiments, all of the standoffs 380 may be similarly sized and/or shaped. In some embodiments, the supports 365 may comprise a diameter from approximately two to four millimeters and/or a height from approximately two to five millimeters.

In some embodiments, the first plurality of supports 1425 may be aligned with and in stacked relationship with the second plurality of supports 1430, and the installation pathway 1525 may be located between at least some of the stacked first plurality of supports 1425 and second plurality of supports 1430. In some embodiments, the first plurality of supports 1425 and the second plurality of supports 1430 may work together to jointly support the negative-pressure pathway 1405. For example, the first plurality of supports 1425 may be stacked and opposingly aligned with the second plurality of supports 1430. In some embodiments, the first spacer layer 1005 and second spacer layer 1010 may be stacked, with the installation pathway 1525 sandwiched therebetween. For example, the first plurality of supports 1425 of the first spacer layer 1005 may be stacked with the second plurality of supports 1430 of the second spacer layer 1010, with supporting faces substantially parallel and/or contacting. In some embodiments, the first plurality of supports 1425 and the second plurality of supports 1430 may jointly support the negative-pressure pathway to maintain an open pathway with a height substantially equal to the height of one of the first plurality of supports 1425 and one of the second plurality of supports 1430 taken together (e.g. stacked to provide a cumulative height). In some embodiments, the installation pathway 1525 may be located between and in stacked relationship with at least some of the first plurality of supports 1425 and at least some of the second plurality of supports 1430, for at least a portion of the negative-pressure pathway 1405.

Figure 15C:
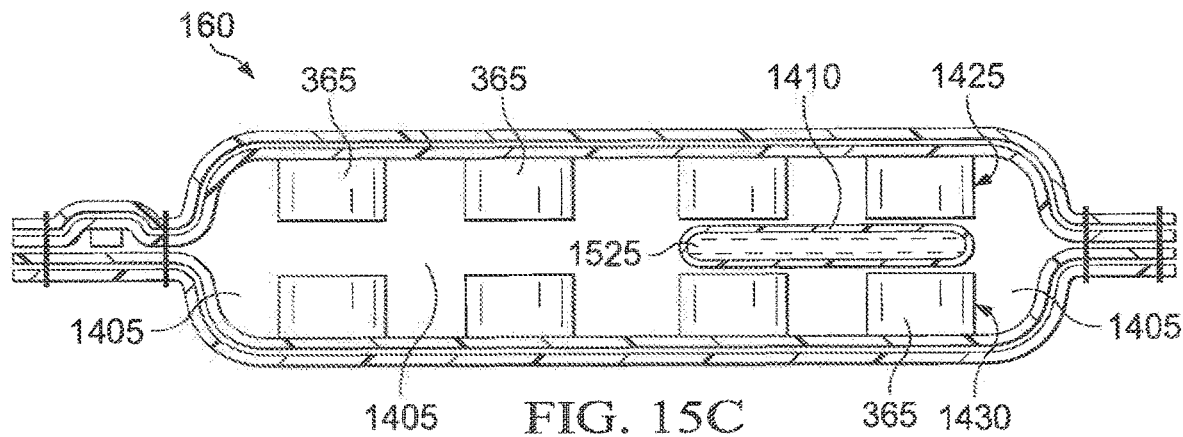
FIG. 15C is a schematic cross-section view of the bridge of FIG. 15A, illustrating instillation when negative pressure is off.

FIG. 15C is a schematic horizontal cross-section view of the bridge 160 of FIG. 15A, illustrating additional details that may be associated with some embodiments. Some embodiments of the negative-pressure pathway 1405 may be similar to the third pathway 350 of FIG. 3A and/or the third fluid conductor 1125 of FIG. 11A. In some embodiments, the negative-pressure pathway 1405 may be configured to maintain an open pathway despite application of negative-pressure and/or external compression loading. In some embodiments, the plurality of supports 365 are configured to maintain the negative-pressure pathway 1405 as an open pathway, for example allowing negative pressure to be applied to a tissue site through the negative-pressure pathway even when the negative-pressure pathway 1405 experiences compressive loads. For example, the negative-pressure pathway 1405 may be maintained in an open position, without collapsing in a way that may close off the negative-pressure pathway 1405, even if the patient is lying atop the bridge 160. In some embodiments, the installation pathway 1525 may be configured with respect to the negative-pressure pathway 1405 so that the supports 365 of the negative-pressure pathway 1405 also ensure that the installation pathway 1525 remains at least partially open for installation. For example, the installation pathway 1525 within the installation conduit 1410 may be located with respect to the supports 365 of the negative-pressure pathway 1405 so that at least a portion of the installation pathway 1525 may be maintained as open between the supports 365 during installation, allowing installation fluid flow through the installation pathway 1525 even when the patient is lying atop the bridge 160. In some embodiments, the plurality of supports 365 may be configured to support the negative-pressure pathway 1405 substantially along its entire length and/or width. For example, the supports 365 may be co-extensive with the negative-pressure pathway 1405. In some embodiments, the supports 365 may be sealed to maintain an internal pressure. For example, the supports 365 may be maintained at a pressure at or above atmospheric pressure, which may aid in resisting compression or collapse.

As shown in in FIG. 15C, the installation pathway 1525 may span a portion, but not all, of the width of the negative-pressure pathway 1405. In some embodiments, at least a portion of the first plurality of supports 1425 may be located on the opposite side of the installation pathway 1410 from at least a portion of the second plurality of supports 1430. The remainder of the negative-pressure pathway 1405 may comprise another portion of the first plurality of supports 1425 stacked directly adjacent to another portion of the second plurality of supports 1430 (e.g. without the installation pathway 1410 therebetween). For example, the installation pathway 1525 may span the widths of two or more supports 365. In some embodiments, at least a portion of the installation pathway 1525 may span one or more spaces between two or more rows of supports 365. In some embodiments, the installation pathway 1525 may span substantially the entire width of the negative-pressure pathway 1405. In the example of FIG. 15C, the installation pathway 1525 may be located within an expandable conduit. For example, the conduit may typically be substantially flat when no installation fluid is located within it, but may expand out to open when installation fluid flow is present.

FIG. 15C illustrates installation through the installation pathway 1525 when there is no compression applied to the bridge 160. The instillation pathway 1525 in FIG. 15C may expand and/or open during instillation fluid flow, for example pushing the first plurality of supports 1425 away from the second plurality of supports 1430. Instillation fluid may then be pumped through the instillation pathway 1525.

Figure 15D:
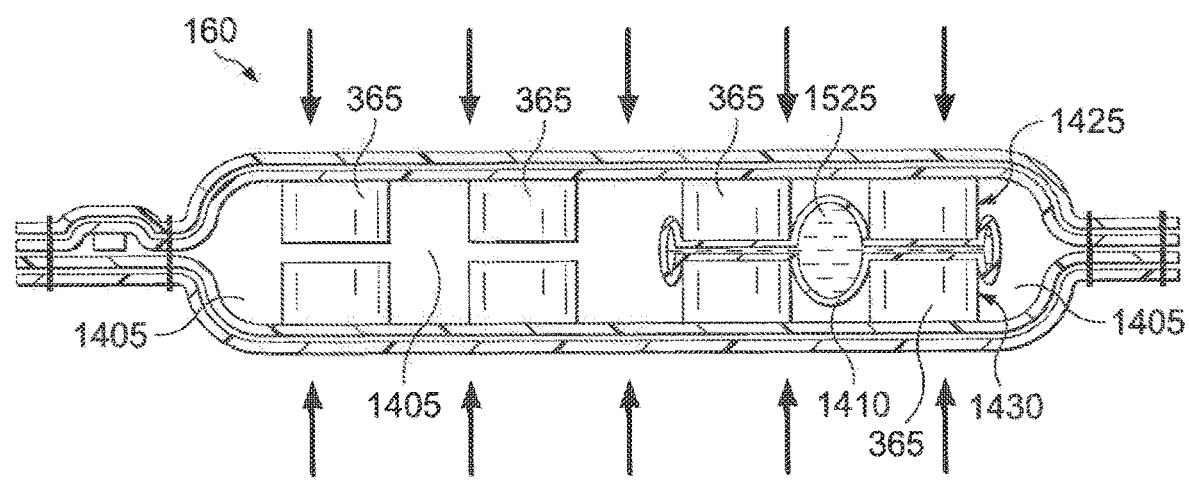
FIG. 15D is a schematic cross-section view of the bridge of FIG. 15A, illustrating instillation when the bridge is under compression.

FIG. 15D is a schematic cross-section view of the bridge 160 of FIG. 15A, illustrating additional details that may be associated with some embodiments. In the example of FIG. 15D, the instillation pathway 1525 may be configured to expand and/or open when the bridge 160 is under compression, to substantially fill spaces between the rows of supports 365 during instillation. This configuration may allow instillation even when the bridge 160 is under compression, ensuring that an open instillation pathway 1525 may be maintained despite compression. For example, the tube-like conduit of the instillation pathway 1525 may interact with the plurality of supports 365 so that the instillation conduit 1410 expands and/or opens into the spaces between the rows of supports 365, thereby allowing longitudinal fluid flow through at least a portion of the instillation pathway 1525 even when the bridge 160 is under sufficient compression so that the first plurality of supports 1425 and the second plurality of supports 1430 are in close proximity (e.g. substantially contacting). In some embodiments, the portions of the instillation pathway 1525 between the first plurality of supports 1425 and the second plurality of supports 1430 might be compressed flat between opposing supports 365 during compression, but the portions of the instillation pathway 1525 between the rows of supports 365 may expand and/or open to substantially fill longitudinally extending spaces between the rows of supports 365 during instillation.

Figure 15E:
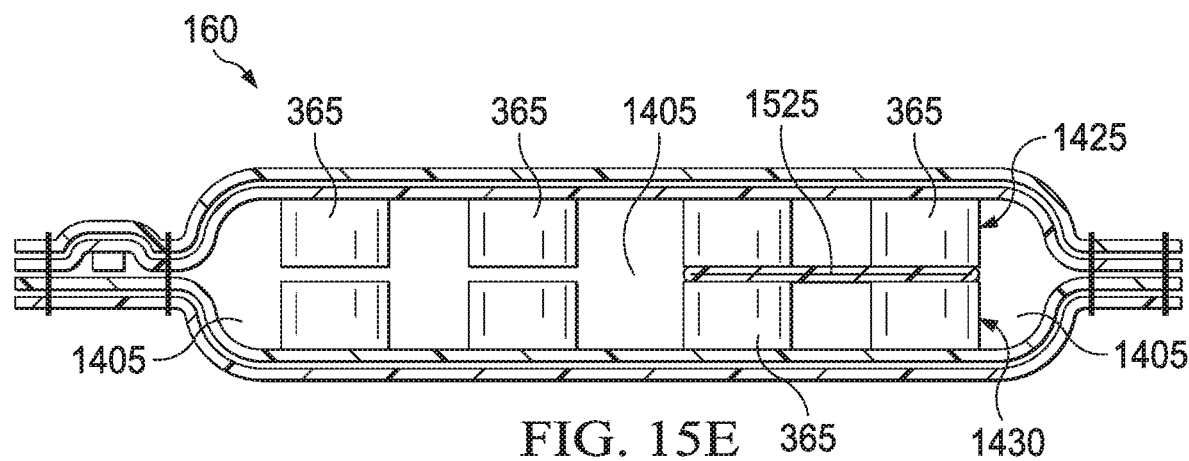
FIG. 15E is a schematic cross-section view of the bridge of FIG. 15A, illustrating negative pressure application when instillation is off.

FIG. 15E is a schematic cross-section view of the bridge 160 of FIG. 15A, illustrating additional details that may be associated with some embodiments. In the example of FIG. 15E, instillation is not occurring. Rather, negative pressure is being applied to the negative-pressure pathway 1405. The instillation pathway 1525 may collapse to be substantially flat and/or closed during negative-pressure therapy. For example, the portions of the instillation pathway 1525 clamped between opposingly aligned supports 365 may be substantially flat, and the portions of the instillation pathway 1525 spanning the spaces between the opposingly aligned supports 365 may also be drawn substantially flat due to negative pressure. For example, communication of negative pressure into the instillation pathway 1525 from the negative-pressure pathway 1405 during negative-pressure therapy may flatten the instillation pathway 1525. This configuration may maximize flow capability through the negative-pressure pathway 1405 during negative-pressure therapy by minimizing the size of the instillation pathway 1525 at such time. During negative-pressure therapy, fluid may be removed through the longitudinally extending rows between the plurality of supports 365, with only minor flat-profile disruption in spaces spanned by the flattened instillation pathway 1525. In some embodiments, the flat configuration of the instillation pathway 1525 during negative-pressure therapy may result in substantially no blockage of flow through the negative-pressure pathway 1405 during fluid removal. This may be true whether or not external compression is applied to the bridge 160. During negative-pressure therapy in some embodiments, the first plurality of supports 1425 may be drawn towards the second plurality of supports 1430, so that the supporting faces substantially contact. For example, some supporting faces of supports 365 may directly contact opposing support faces, while some supports 365 may only be separated from opposingly aligned supports 365 by a substantially flat instillation pathway 1525.

Figure 16:
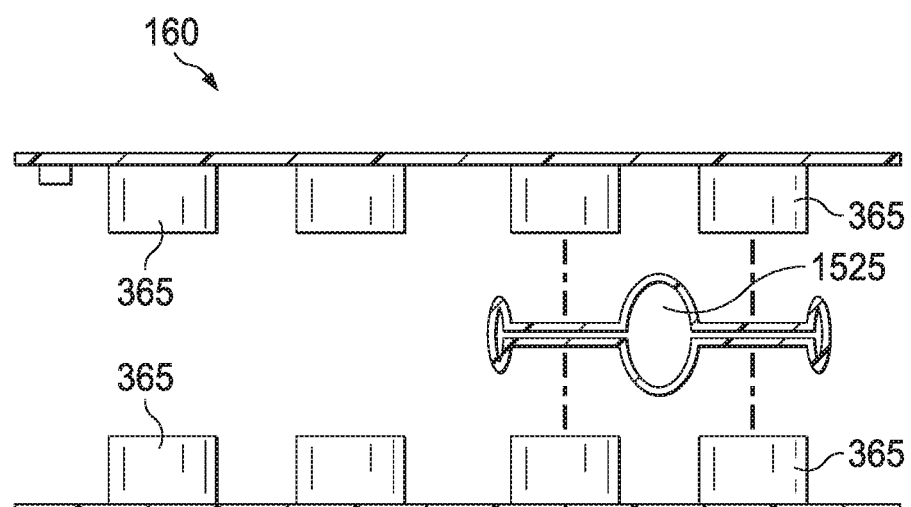
FIG. 16 is a partial assembly schematic view illustrating another example of an instillation conduit.

FIG. 16 is a partial assembly schematic view of another, similar bridge 160, illustrating additional details that may be associated with some embodiments. In some embodiments, the instillation pathway 1525 may have a shape matching the supports 365 spanning at least a portion of the width of the negative-pressure pathway 1405. In some embodiments, the instillation pathway 1525 may have a corrugated shape, for example flat where interacting with a row of supports 365, and non-flat (e.g. shaped or capable of expanding and/or opening to allow fluid flow) in spaces between rows of supports 365. Shaped instillation pathway embodiments may still be configured to be collapsible, however, in order to prevent siphoning of fluid during negative-pressure therapy. In some embodiments, the instillation pathway 1525 may comprise a plurality of collapsible longitudinal conduits located between the supports 365 in the enclosed space of the negative-pressure pathway 1405.

In some embodiments, the instillation pathway may be located in a separate bridge from the negative-pressure pathway. In such embodiments, the instillation pathway may still be configured to interact with the negative-pressure pathway, for example by fluid communication therebetween, so that at least a portion of the instillation pathway collapses upon application of negative pressure to the separate negative-pressure pathway.

Figure 17:
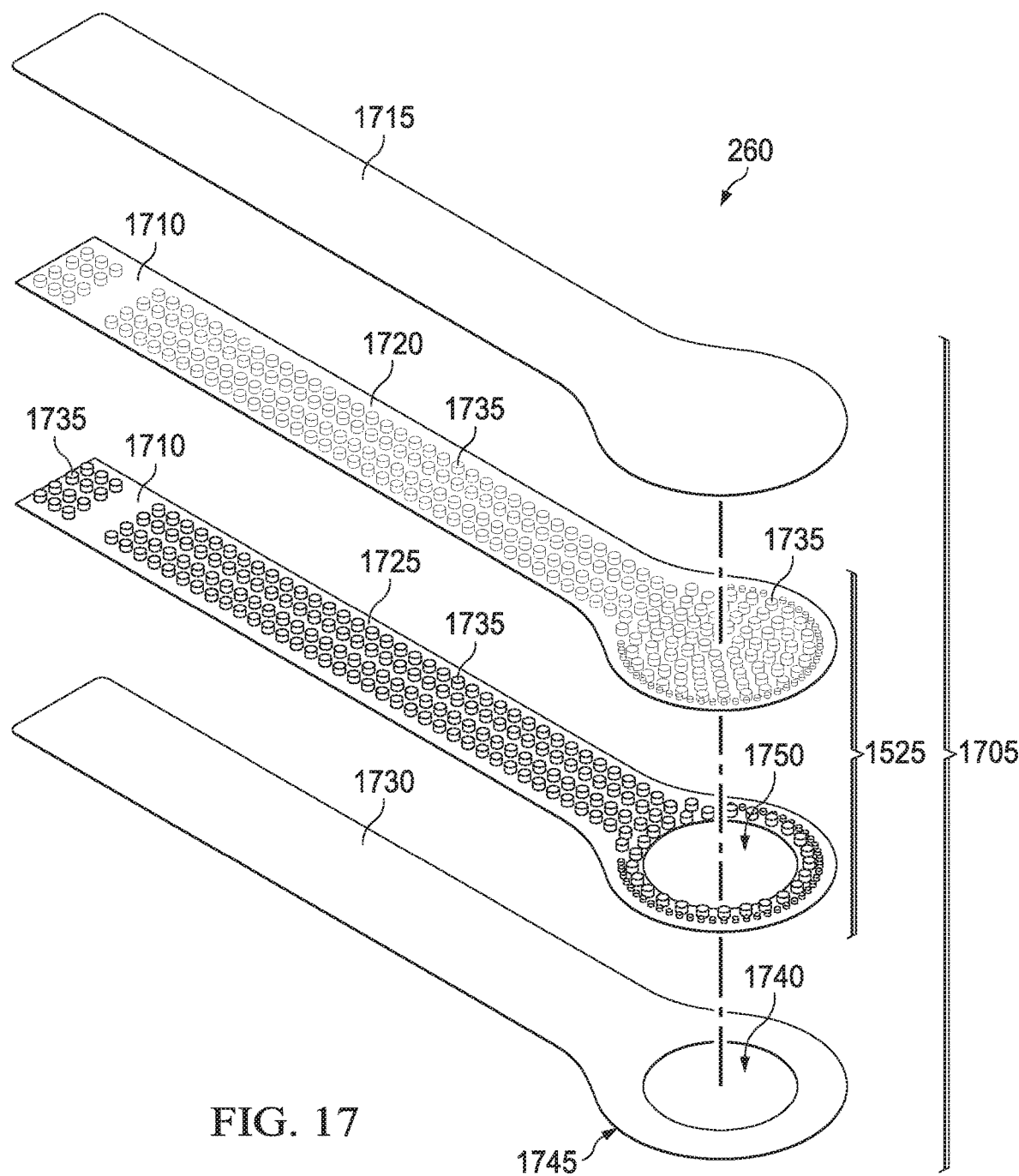
FIG. 17 is an assembly view of an example of a different type of bridge for instillation.

FIG. 17 is an assembly view of an example of the dressing interface 260 for instillation that may be associated with some example embodiments of the therapy system 100. In some embodiments, the dressing interface 260 may comprise an instillation bridge 1705. The instillation bridge 1705 may be similar to the bridge 160 of FIG. 10 in construction, but may comprise a gap 1710 in the open pathway of the instillation bridge 1705 with no supports. In some embodiments, the instillation bridge 1705 may be configured to provide instillation but not negative pressure. In some embodiments, the instillation bridge 1705 may be configured to allow application of instillation fluid during instillation, but to minimize or prevent siphoning of instillation fluid during negative-pressure therapy (for example administered through a separate negative-pressure bridge).

In some embodiments, the instillation bridge 1705 may comprise a first instillation layer 1715, a first instillation spacer layer 1720, a second instillation spacer layer 1725, and a second instillation layer 1730. In FIG. 17, the first instillation spacer layer 1720 and the second instillation spacer layer 1725 may be stacked adjacent one another with instillation supports 1735 facing inward and/or contacting. For example, the instillation pathway 1525 may comprise a first instillation spacer layer 1720 and a second instillation spacer layer 1725, each having instillation supports 1735 projecting inward into an enclosed space of the instillation pathway 1525. The first instillation layer 1715 may be adjacent to and in stacked relationship with the first instillation spacer layer 1720, opposite the second instillation support layer 1725. The second instillation layer 1730 may be adjacent to and in stacked relationship with the second instillation spacer layer 1725, opposite the first instillation spacer layer 1720. The first instillation layer 1715 and the second instillation layer 1730 may be sealed together about the perimeter, forming the enclosed instillation pathway 1525 supported by the first instillation spacer layer 1720 and the second instillation spacer layer 1725.

In FIG. 17, the second instillation layer 1730 may comprise an instillation aperture 1740 configured to allow fluid communication between the instillation pathway 1525 and the ambient environment. The instillation aperture 1740 in FIG. 17 may be located in a distal end 1745 of the instillation bridge 1705. Some embodiments may also comprise a second instillation aperture 1750 located in the second instillation spacer layer 1725 which may be concentric with the instillation aperture 1740. In some embodiments, the first instillation layer 1715 and the second instillation layer 1730 may each be formed of a film. Other embodiments may form the instillation pathway 1525 as an open pathway using only a single spacer layer. Other embodiments may form the instillation pathway 1525 by sealing the first instillation spacer layer 1720 to the second instillation spacer layer 1725 about the perimeter, for example without the need for any exterior film layers. Other embodiments may form the instillation pathway 1525 between the first instillation layer 1715 and the second instillation layer 1730, while having the plurality of instillation supports located therebetween without any instillation spacer layers. For example, longitudinal tubular supports might be located between the first instillation layer 1715 and the second instillation layer 1730 in some alternate embodiments.

In some embodiments, the first instillation layer 1715 and/or the second instillation layer 1730 may comprise a polyurethane film from approximately 80 to 120 micron in thickness. In some embodiments, the first instillation spacer layer 1720 and/or the second instillation spacer layer 1725 may be thermoformed structures with integral open pathway features, such as instillation supports 1735. In some embodiments, the thermoformed structures may comprise thermoplastic polyurethane, for example thermoplastic polyurethane film from approximately 200 to 500 microns in thickness. Some embodiments of the dressing interface 260 may be configured with a low profile. For example, the dressing interface 260 may be configured as a low-profile instillation bridge 1705, which may have a height of approximately 5 millimeters or less.

FIG. 18A is a plan view of the instillation bridge 1705 of FIG. 17, illustrating additional details that may be associated with some embodiments. In some embodiments, the instillation pathway 1525 may extend from an instillation port 1805 to the instillation aperture in the distal end 1745 of the instillation bridge 1705. In some embodiments, the plurality of instillation supports 1735 may be arranged in rows, and the rows may be aligned. For example, the rows may be aligned to extend longitudinally for approximately the entire length of the instillation bridge 1705. In the example shown in FIG. 18A, longitudinally extending spaces may separate the rows of instillation supports 1735, providing unobstructed channels for fluid flow during instillation. In some embodiments, the longitudinally extending spaces may extend substantially from the instillation port 1805 to the instillation aperture 1740.

As shown in FIG. 18A, the instillation pathway 1525 may have a portion without any supports, forming a gap 1710 in the supports of the open pathway. For example, the gap 1710 may span the width of the instillation pathway 1525 and provide no support across such width. In some embodiments, except for the gap 1710, the plurality of instillation supports 1735 may be co-extensive with the instillation pathway 1525. For example, the instillation supports 1735 may span substantially the width and length of the instillation pathway 1525, except for the gap 1710 (which may be unsupported). Except for the presence of the gap 1710, some embodiments of the instillation bridge 1705 may be similar in material and/or construction to the negative-pressure bridge 160 of FIG. 10. The gap 1710 in the example of FIG. 18A may be located in proximity to the proximal end 1810 and/or the instillation port 1805. In other embodiments, the gap 1710 may be located at different positions along the length of the instillation pathway 1525, for example in proximity to the distal end 1745 and/or the instillation aperture. In some embodiments, the instillation pathway 1525 may have two or more gaps 1710, for example positioned at various locations along the length of the instillation pathway 1525.

FIG. 18B is a schematic longitudinal cross-section slice view of a portion of the bridge 160 of FIG. 18A, illustrating additional details that may be associated with some embodiments. As shown in FIG. 18B, the first instillation spacer layer 1720 and the second instillation spacer layer 1725 may each have a portion without instillation supports, which may jointly form the gap 1710. The instillation pathway 1525 may be pneumatically isolated from the ambient environment except through the instillation aperture 1740 in the distal end 1745 of the instillation bridge 1705. The plurality of instillation supports 1735 within the instillation pathway 1525 may be configured to support the instillation pathway 1525, except for the gap 1710 between the plurality of instillation supports 1735. The gap 1710 may be configured to allow collapse across the width of the instillation pathway 1525 upon application of negative pressure. For example, the gap 1710 may not have any instillation supports 1735. Collapse of the gap 1710 in the instillation pathway 1525 may be sufficient to close the instillation pathway 1525, substantially preventing fluid flow through the instillation pathway 1525 and/or substantially preventing siphoning of instillation fluid upon application of negative pressure. The installation supports 1735 may be similar to the plurality of supports 365 in FIG. 10, in some embodiments.

Figure 18C:
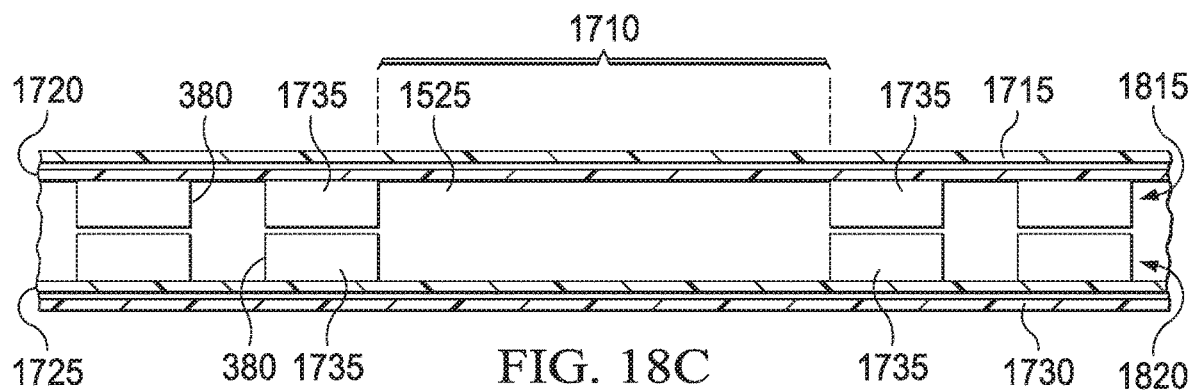
FIG. 18C is a schematic cross-section view of a portion of the instillation bridge of FIG. 18A, illustrating instillation.

FIG. 18C is a schematic view of a portion of the instillation bridge 1705 of FIG. 18A, illustrating additional details that may be associated with some embodiments. As FIG. 18C illustrates, in some embodiments the instillation bridge 1705 may comprise a first instillation layer 1715 and a second instillation layer 1730, which may be coupled to form an enclosed space of the instillation pathway 1525 between the first instillation layer 1715 and the second instillation layer 1730. The plurality of instillation supports 1735 may be located between the first instillation layer 1715 and the second instillation layer 1730. In some embodiments, the plurality of instillation supports 1735 may comprise a first plurality of instillation supports 1815 and a second plurality of instillation supports 1820. For example, the first plurality of instillation supports 1815 may extend inward from an inner surface of the first instillation spacer layer 1720; and the second plurality of instillation supports 1820 may extend inward from an inner surface of the second instillation spacer layer 1725. In some embodiments, the first plurality of instillation supports 1815 and the second plurality of instillation supports 1820 may be aligned and stacked, for example jointly supporting the instillation pathway 1525. In some embodiments, the first plurality of instillation supports 1815 and the second plurality of instillation supports 1820 may each be aligned into longitudinally extending rows. For example, the first plurality of instillation supports 1815 may be aligned into rows that match the rows of the second plurality of instillation supports 1820, so that the first plurality of instillation supports 1815 may be opposingly aligned and stacked with the second plurality of instillation supports 1820. In some embodiments, the first plurality of instillation supports 1815 and the second plurality of instillation supports 1820 may jointly support the instillation pathway 1525 to maintain an open pathway with a height substantially equal to the height of one of the first plurality of instillation supports 1815 and one of the second plurality of instillation supports 1820 taken together (e.g. stacked to provide a cumulative height).

In some embodiments, the first instillation layer 1715 may be sealed to the first instillation spacer layer 1720, and the second instillation layer 1730 may be sealed to the second instillation spacer layer 1725. For example, each of the first plurality of instillation supports 1815 of the first instillation spacer layer 1720 may comprise a hollow standoff 380, and the first instillation layer 1715 may be sealed to the first instillation spacer layer 1720 to maintain internal pressure within the plurality of hollow standoffs 380 of the first instillation spacer layer 1720. Each of the second plurality of instillation supports 1820 of the second instillation spacer layer 1725 may comprise a hollow standoff 380, and the second instillation layer 1730 may be sealed to the second instillation spacer layer 1725 to maintain internal pressure within the plurality of hollow standoffs 380 of the second instillation spacer layer 1725. In some embodiments, each of the plurality of instillation supports 1735 may comprise a standoff 380 and a base, with the standoff 380 having a closed surface extending away from the base. An opening in the base may be sealed by a film attached to the base, for example maintaining internal pressure within the hollow standoffs 380. The instillation supports 1735 may comprise a variety of shapes, for example substantially circular, hexagonal, oval, triangular, and/or square. In some embodiments, the standoffs 380 of the first instillation spacer layer 1720 and/or the second instillation spacer layer 1725 may each comprise a blister, a bubble, or a cell. In some embodiments, all of the standoffs 380 may be similarly sized and/or shaped. In some embodiments, the instillation supports 1735 may comprise a diameter from approximately two to four millimeters and/or a height from approximately two to five millimeters.

FIG. 18C illustrates the instillation pathway 1525 of FIG. 18A during instillation and/or when there is no negative pressure applied, and the gap 1710 is in an open configuration. For example, the fluid pressure during instillation may ensure that the gap 1710 does not collapse. The gap 1710 without supports may operate as shown in FIG. 18C to allow fluid flow through an open pathway during instillation. In some embodiments, the instillation pathway 1525 may be configured to allow instillation even when under compression. For example, the instillation supports 1735 may support the instillation pathway 1525 to maintain an open pathway for instillation even under compression.

Figure 18D:
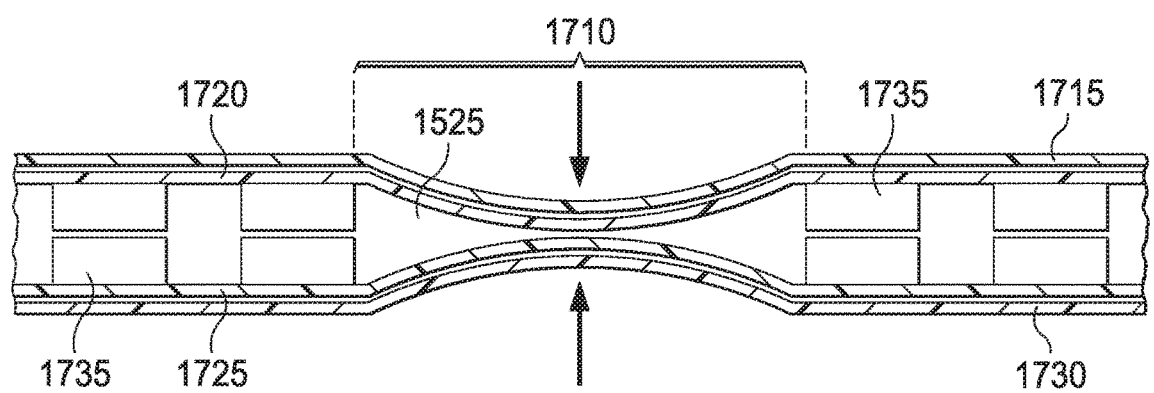
FIG. 18D is a schematic cross-section view of a portion of the instillation bridge of FIG. 18A, illustrating negative pressure.

FIG. 18D is a schematic view of a portion of the instillation bridge 1705 of FIG. 18A, illustrating additional details that may be associated with some embodiments. FIG. 18D illustrates the instillation bridge 1710 when experiencing negative-pressure in the instillation pathway 1525. As FIG. 18D illustrates, in some embodiments when negative pressure is applied to the instillation pathway 1525, the negative pressure may cause the gap 1710 to collapse. For example, the negative pressure within the instillation pathway 1525 may draw the first instillation layer 1715 and the second instillation layer 1730 (and/or the first instillation spacer layer 1720 and the second instillation spacer layer 1725) together at the gap 1710, closing off the instillation pathway 1525 to restrict or prevent fluid flow therethrough. The gap 1710 may flex inward to collapse across the width of the instillation pathway 1525 upon application of negative pressure, to close the instillation pathway 1525. For example, the gap 1710 in FIG. 18D is shown in a closed configuration. Collapse of the gap 1710 in the instillation pathway 1525 may be sufficient to close the instillation pathway 1525, substantially preventing fluid flow through the instillation pathway 1525 and/or substantially preventing siphoning of instillation fluid upon application of negative pressure.

Upon removal of the negative pressure, the instillation pathway 1525 may re-open in some embodiments, for example with the first instillation layer 1715 and the second instillation layer 1730 (and/or the first instillation spacer layer 1720 and the second instillation spacer layer 1725) at the gap 1710 flexing or springing back to the open position shown in FIG. 18C. For example, the gap may re-open to have a height substantially similar to that of the remainder of the instillation pathway 1525. In some embodiments, providing or pumping instillation fluid to the instillation pathway 1525 may re-open the gap 1710. In some embodiments, the gap 1710 may be located with instillation supports 1735 on both sides of the gap 1710, for example proximally and distally. In some embodiments, the gap 1710 may be sized large enough to allow sufficient flexing to close, while also being sized small enough so that the instillation supports 1735 may prevent collapse of the gap 1710 due to external compression loading (for example if a patient lies atop the instillation bridge 1705). For example, the instillation pathway 1525 of the installation bridge 1705 may be configured to maintain an open fluid pathway when fluid is applied therethrough. The instillation pathway 1525 may also be configured to interact with the negative-pressure pathway of a separate negative-pressure bridge through the instillation aperture 1740 so that, upon application of negative pressure, at least a portion (e.g. the gap 1710) of the instillation pathway 1525 collapses. For example, negative pressure applied to the instillation pathway 1525 of the instillation bridge 1705 may cause collapse and closing of the gap 1710. Negative pressure may be applied to the instillation pathway 1525 through the instillation aperture in some embodiments.

Figure 19:
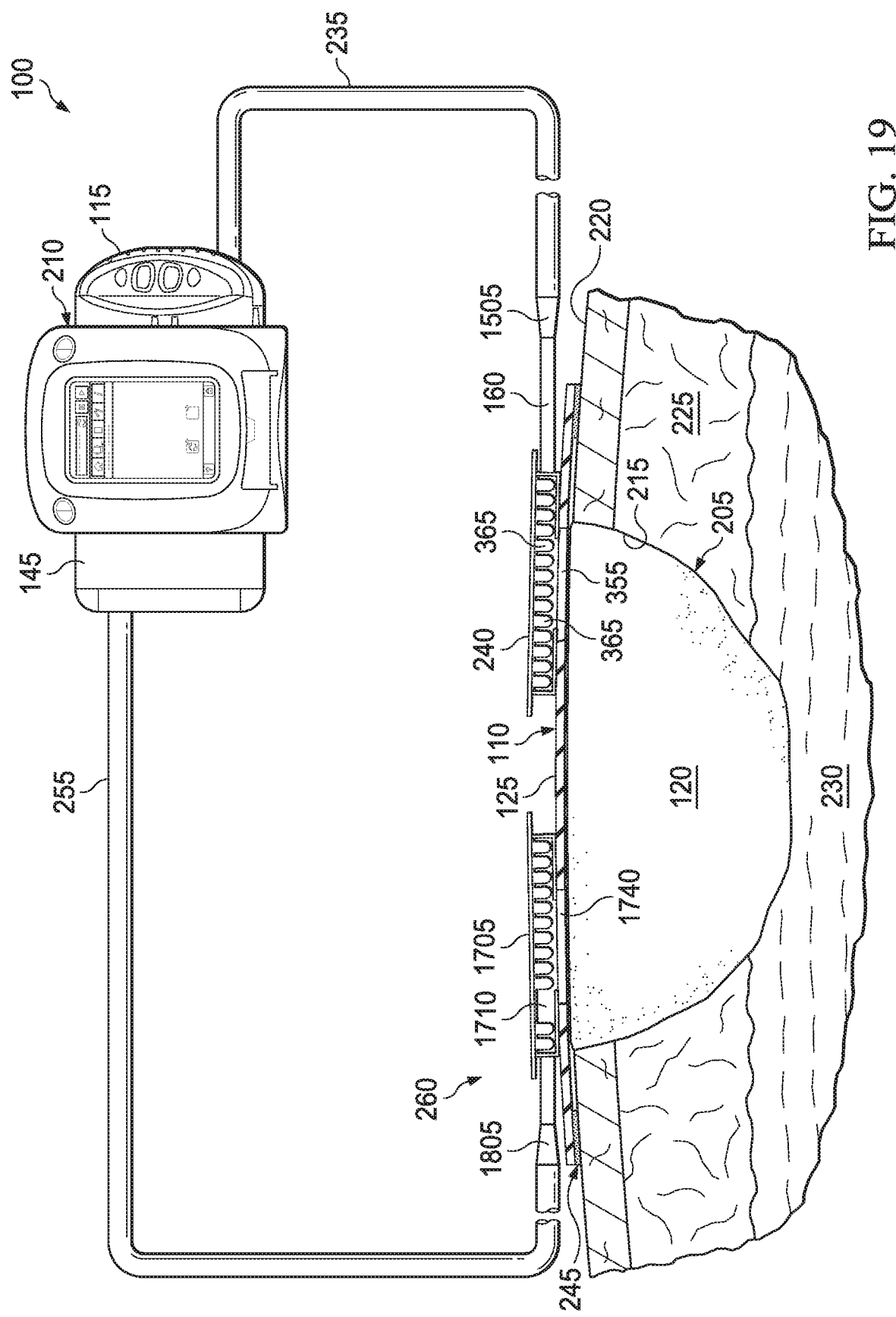
FIG. 19 is a schematic view of another example embodiment of the therapy system of FIG. 1 configured to apply negative pressure and treatment solution to a tissue site using separate bridges for negative pressure and instillation.

FIG. 19 is a schematic diagram of another example embodiment of the therapy system 100 configured to apply negative pressure and treatment solution to a tissue site 205. For example, the therapy system 100 shown in FIG. 19 may include two separate low-profile bridges, such as the bridge 160 for application of negative pressure to the tissue site 205, and the instillation bridge 1705 for application of instillation fluid to the tissue site 205. For example, the dressing interface 260 of the system may comprise the instillation bridge 1705. Some embodiments of the system may comprise a negative-pressure delivery system, such as negative-pressure bridge 160, that comprises a negative-pressure pathway that is pneumatically isolated from the ambient environment and from the instillation bridge 1705 except through an aperture 355 in a distal end of the negative-pressure pathway; and the instillation bridge 1705 of FIG. 17.

In some embodiments, the negative-pressure pathway may comprise supports 365. For example, the supports 365 may be co-extensive with the negative-pressure pathway. In some embodiments, the instillation pathway of the instillation bridge 1705 may be configured to interact with the negative-pressure pathway so that, upon application of negative pressure to the negative-pressure pathway, the gap 1710 collapses to close the instillation pathway of instillation bridge 1705. For example, the aperture 355 of the negative-pressure pathway and the instillation aperture 1740 of the instillation pathway may both be in fluid communication with the tissue site 205, and negative pressure applied to the negative-pressure pathway may be in fluid communication with the instillation pathway through the tissue site 205. Collapse of the gap 1710 of the instillation pathway, for example due to application of negative pressure, may be sufficient to close the instillation pathway and/or prevent siphoning of instillation fluid when negative pressure is applied to the negative-pressure pathway in some embodiments, substantially preventing fluid flow through the instillation pathway.

In some embodiments, the instillation pathway of the instillation bridge 1705 may be in fluid communication with a solution source 145, while the negative-pressure pathway of the negative-pressure bridge 160 may be in fluid communication with a negative-pressure source 105. For example, the instillation port 1805 of the instillation pathway may be in fluid communication with the solution source 145, and the port 1505 of the negative-pressure pathway may be in fluid communication with the negative-pressure source 105. In some embodiments, the instillation pathway may be located in a separate bridge (e.g. instillation bridge 1705) from the negative-pressure pathway (e.g. located in negative-pressure bridge 160), as shown in FIG. 19. In some embodiments, the instillation pathway may be configured to maintain an open fluid pathway when fluid is applied therethrough and/or when there is no negative pressure (for example, despite external compression loading). In some embodiments, the negative-pressure pathway may be configured to maintain an open pathway despite application of negative-pressure and/or external compression loading. Each of the instillation bridge 1705 and the negative-pressure pathway bridge 160 may be configured with a low profile, in some embodiments.

The systems, apparatuses, and methods described herein may provide significant advantages. For example, some embodiments may maintain separate instillation and negative-pressure treatment pathways. Some embodiments may have a low-profile and/or be conformable, for improved comfort if positioned under a patient for example. Some embodiments may be configured to prevent occlusion, maintaining an open pathway for negative-pressure treatment and/or instillation fluid delivery so that the negative pressure and/or instillation fluid may be provided even when the device is under compressive load (for example, if the patient is lying atop the device). Some embodiments may improve access to certain wound sites. Some embodiments may be configured to minimize unintended siphoning of instillation fluid during negative-pressure treatment. The configuration of some embodiments may reduce contamination of instillation fluid, for example by preventing exudate from flowing into the instillation system. Some embodiments may allow wound pressure monitoring, which may for example reduce the risk of pressure drop between the pad and the wound. Some embodiments may employ a single bridge which contains both the negative-pressure pathway and the instillation pathway, which may simplify installation and use.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the bridge 160 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for managing fluid at a tissue site, the apparatus comprising:
   a negative-pressure pathway comprising a first layer and a second layer being coupled to each other to form an enclosed space between the first layer and the second layer, and a first spacer layer and a second spacer layer;
   a plurality of supports disposed within the enclosed space between the first layer and the second layer, the plurality of supports comprises a first plurality of supports extending inward from the first spacer layer and a second plurality of supports extending inward from the second spacer layer configured to support the negative-pressure pathway; and
   an instillation pathway, wherein the instillation pathway is located between the first spacer layer and the second spacer layer, and wherein the instillation pathway is further located between the first plurality of supports and the second plurality of supports configured to interact with the negative pressure pathway so that at least a portion of the instillation pathway collapses upon application of the negative pressure to the negative-pressure pathway, the instillation pathway comprising a collapsible conduit configured to interact with the plurality of supports so that the collapsible conduit collapses along its length upon application of negative pressure to the negative-pressure pathway.

2. The apparatus of claim 1, wherein:
   the negative-pressure pathway further comprises a recessed space in a distal end; and
   the negative-pressure pathway and the instillation pathway are pneumatically isolated from each other except through the recessed space.

3. The apparatus of claim 1, wherein:
   each of the plurality of supports comprises a hollow standoff; and
   each of the standoffs is sealed to maintain an internal pressure.

4. The apparatus of claim 1, wherein the instillation pathway is located within the negative-pressure pathway and extends lengthwise substantially for the length of the negative-pressure pathway.

5. The apparatus of claim 2, wherein:
   the negative-pressure pathway further comprises an aperture; and
   the recessed space is in fluid communication with an ambient environment through the aperture.

6. The apparatus of claim 1, wherein:
   the negative-pressure pathway further comprises a spacer layer; and the plurality of supports extend from an inner surface of the spacer layer.

7. The apparatus of claim 6, wherein:
each of the plurality of supports comprises a hollow standoff; and
the first layer further comprises a first film sealed to the spacer layer to maintain internal pressure within the plurality of standoffs.

8. The apparatus of claim 1, wherein:
the plurality of supports further comprises a first plurality of supports and a second plurality of supports;
the first plurality of supports are aligned with and in stacked relationship with the second plurality of supports; and
the instillation pathway is located between at least some of the stacked first plurality of supports and second plurality of supports.

9. The apparatus of claim 1, wherein:
the negative-pressure pathway further comprises an aperture; and
the instillation pathway and the negative-pressure pathway are in fluid communication with an ambient environment through the aperture.

10. The apparatus of claim 1, wherein:
each of the first plurality of supports comprises one of a first plurality of hollow standoffs; and
each of the second plurality of supports comprises one of a second plurality of hollow standoffs.

11. The apparatus of claim 1, wherein:
the first plurality of supports are aligned with and in stacked relationship with the second plurality of supports; and
the instillation pathway is located between at least some of the stacked first plurality of supports and second plurality of supports.

12. The apparatus of claim 1, wherein the plurality of supports in the negative-pressure pathway are configured with respect to the instillation pathway to ensure that the instillation pathway is operable for instillation fluid flow when external compression force is upon the apparatus.

13. The apparatus of claim 1, further comprising a pressure sensing pathway that extends parallel to the negative-pressure pathway.

14. The apparatus of claim 13, further comprising:
a port configured to fluidly couple the negative-pressure pathway to a negative pressure source and fluidly couple the instillation pathway to an instillation source, the port being located in a proximal end of the apparatus;
wherein the port is further configured to fluidly couple the pressure sensing pathway to a pressure sensor;
an aperture, the instillation pathway and the negative-pressure pathway being in fluid communication with an ambient environment through the aperture; and
the pressure sensing pathway extends from the port to the aperture.

15. The apparatus of claim 13, further comprising:
a recessed space in a distal end of the negative-pressure pathway; and
a barrier between the inner surface of the first layer and the inner surface of the second layer to form the pressure sensing pathway within the enclosed space of the negative-pressure pathway;
wherein the pressure sensing pathway is pneumatically isolated from the negative-pressure pathway and the instillation pathway except through the recessed space in the distal end.

* * * * *